(12) United States Patent
Dietz et al.

(10) Patent No.: US 8,961,547 B2
(45) Date of Patent: Feb. 24, 2015

(54) ULTRASONIC SURGICAL INSTRUMENTS WITH MOVING CUTTING IMPLEMENT

(75) Inventors: Timothy G. Dietz, Terrace Park, OH (US); Gregory W. Johnson, Milford, OH (US); Sean P. Conlon, Loveland, OH (US); Daniel J. Mumaw, Milford, OH (US); Jerome R. Morgan, Cincinnati, OH (US); William D. Dannaher, Cincinnati, OH (US); Omar J. Vakharia, Cincinnati, OH (US); Richard W. Timm, Cincinnati, OH (US); Matthew C. Miller, Cincinnati, OH (US); Galen C. Robertson, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 163 days.

(21) Appl. No.: 12/703,893

(22) Filed: Feb. 11, 2010

(65) Prior Publication Data
US 2011/0196404 A1    Aug. 11, 2011

(51) Int. Cl.
A61B 17/32    (2006.01)
A61B 17/3207    (2006.01)
A61B 17/22    (2006.01)

(52) U.S. Cl.
CPC ... *A61B 17/320783* (2013.01); *A61B 17/22004* (2013.01); *A61B 17/320068* (2013.01); *A61B 17/3207* (2013.01)
USPC .......................................... 606/169; 604/22

(58) Field of Classification Search
CPC ..................... A61B 17/22004; A61B 17/3207
USPC .............. 606/27, 159, 169, 170–171; 604/22; 600/437; 30/346.55
See application file for complete search history.

(56) References Cited

U.S. PATENT DOCUMENTS

| 969,528 A | 9/1910 | Disbrow |
| 1,570,025 A | 1/1926 | Young |
| 2,704,333 A | 3/1955 | Calosi et al. |

(Continued)

FOREIGN PATENT DOCUMENTS

| CN | 1634601 a | 7/2005 |
| CN | 1640365 A | 7/2005 |

(Continued)

OTHER PUBLICATIONS

Technology Overview, printed from www.harmonicscalpel.com, Internet site, website accessed on Jun. 13, 2007, (3 pages).

(Continued)

*Primary Examiner* — Victor Nguyen

(57) ABSTRACT

In various embodiments, a surgical instrument for operation in an aqueous environment is provided. In at least one embodiment, the surgical instrument may include a hollow sheath and a blade disposed at least partially within the sheath. Coupled to the blade may be at least one ultrasonic transducer, which, in turn, may be coupled to a drive system. The drive system may be configured to deliver gross axial motions to the blade such that the blade translates with respect to the hollow sheath when the drive system is activated. Accordingly, tissue may be cut by the blade with gross axial movement of the blade and/or ultrasonic vibrational motion provided by the ultrasonic transducer(s). In alternative embodiments, the blade may be rotated axially instead of translated with respect to the hollow sheath.

14 Claims, 24 Drawing Sheets

(56) References Cited

U.S. PATENT DOCUMENTS

| | | | |
|---|---|---|---|
| 2,736,960 A | 3/1956 | Armstrong | |
| 2,849,788 A | 9/1958 | Creek | |
| RE25,033 E | 8/1961 | Balamuth et al. | |
| 3,015,961 A | 1/1962 | Roney | |
| 3,513,848 A | 5/1970 | Winston et al. | |
| 3,526,219 A | 9/1970 | Balamuth | |
| 3,614,484 A | 10/1971 | Shoh | |
| 3,616,375 A * | 10/1971 | Inoue | 204/157.61 |
| 3,636,943 A | 1/1972 | Balamuth | |
| 3,776,238 A | 12/1973 | Peyman et al. | |
| 3,805,787 A | 4/1974 | Banko | |
| 3,830,098 A | 8/1974 | Antonevich | |
| 3,854,737 A | 12/1974 | Gilliam, Sr. | |
| 3,862,630 A | 1/1975 | Balamuth | |
| 3,900,823 A | 8/1975 | Sokal et al. | |
| 3,918,442 A | 11/1975 | Nikolaev et al. | |
| 3,946,738 A | 3/1976 | Newton et al. | |
| 3,955,859 A | 5/1976 | Stella et al. | |
| 3,956,826 A | 5/1976 | Perdreaux, Jr. | |
| 4,156,187 A | 5/1979 | Murry et al. | |
| 4,188,927 A | 2/1980 | Harris | |
| 4,200,106 A | 4/1980 | Douvas et al. | |
| 4,306,570 A | 12/1981 | Matthews | |
| 4,445,063 A | 4/1984 | Smith | |
| 4,491,132 A | 1/1985 | Aikins | |
| 4,574,615 A | 3/1986 | Bower et al. | |
| 4,617,927 A | 10/1986 | Manes | |
| 4,633,119 A | 12/1986 | Thompson | |
| 4,634,420 A | 1/1987 | Spinosa et al. | |
| 4,640,279 A | 2/1987 | Beard | |
| 4,649,919 A | 3/1987 | Thimsen et al. | |
| 4,708,127 A | 11/1987 | Abdelghani | |
| 4,712,722 A | 12/1987 | Hood et al. | |
| 4,827,911 A | 5/1989 | Broadwin et al. | |
| 4,832,683 A | 5/1989 | Idemoto et al. | |
| 4,838,853 A | 6/1989 | Parisi | |
| 4,850,354 A | 7/1989 | McGurk-Burleson et al. | |
| 4,865,159 A | 9/1989 | Jamison | |
| 4,896,009 A | 1/1990 | Pawlowski | |
| 4,903,696 A | 2/1990 | Stasz et al. | |
| 4,922,902 A | 5/1990 | Wuchinich et al. | |
| 4,965,532 A | 10/1990 | Sakurai | |
| 4,979,952 A | 12/1990 | Kubota et al. | |
| 4,981,756 A | 1/1991 | Rhandhawa | |
| 5,026,387 A | 6/1991 | Thomas | |
| 5,109,819 A | 5/1992 | Custer et al. | |
| 5,112,300 A | 5/1992 | Ureche | |
| 5,123,903 A | 6/1992 | Quaid et al. | |
| 5,126,618 A | 6/1992 | Takahashi et al. | |
| 5,162,044 A | 11/1992 | Gahn et al. | |
| 5,163,537 A | 11/1992 | Radev | |
| 5,167,725 A | 12/1992 | Clark et al. | |
| D332,660 S | 1/1993 | Rawson et al. | |
| 5,176,677 A * | 1/1993 | Wuchinich | 606/46 |
| 5,176,695 E | 1/1993 | Dulebohn | |
| 5,184,605 A | 2/1993 | Grzeszykowski | |
| 5,188,102 A | 2/1993 | Idemoto et al. | |
| 5,213,569 A | 5/1993 | Davis | |
| 5,221,282 A | 6/1993 | Wuchinich | |
| 5,226,909 A | 7/1993 | Evans et al. | |
| 5,226,910 A | 7/1993 | Kajiyama et al. | |
| 5,241,236 A | 8/1993 | Sasaki et al. | |
| 5,257,988 A | 11/1993 | L'Esperance, Jr. | |
| 5,261,922 A | 11/1993 | Hood | |
| 5,263,957 A | 11/1993 | Davison | |
| 5,275,609 A * | 1/1994 | Pingleton et al. | 606/170 |
| 5,282,800 A | 2/1994 | Foshee et al. | |
| 5,304,115 A | 4/1994 | Pflueger et al. | |
| D347,474 S | 5/1994 | Olson | |
| 5,322,055 A | 6/1994 | Davison et al. | |
| 5,324,299 A | 6/1994 | Davison et al. | |
| 5,326,342 A | 7/1994 | Pflueger et al. | |
| 5,344,420 A | 9/1994 | Hilal et al. | |
| 5,346,502 A | 9/1994 | Estabrook et al. | |
| 5,353,474 A | 10/1994 | Good et al. | |
| 5,357,423 A | 10/1994 | Weaver et al. | |
| 5,366,466 A | 11/1994 | Christian et al. | |
| 5,371,429 A | 12/1994 | Manna | |
| D354,564 S | 1/1995 | Medema | |
| 5,381,067 A | 1/1995 | Greenstein et al. | |
| 5,403,312 A | 4/1995 | Yates et al. | |
| 5,411,481 A | 5/1995 | Allen et al. | |
| 5,419,761 A | 5/1995 | Narayanan et al. | |
| 5,421,829 A | 6/1995 | Olichney et al. | |
| 5,438,997 A | 8/1995 | Sieben et al. | |
| 5,449,370 A | 9/1995 | Vaitekunas | |
| 5,471,988 A | 12/1995 | Fujio et al. | |
| 5,483,501 A | 1/1996 | Park et al. | |
| 5,486,162 A | 1/1996 | Brumbach | |
| 5,500,216 A | 3/1996 | Julian et al. | |
| 5,501,654 A | 3/1996 | Failla et al. | |
| 5,505,693 A | 4/1996 | Mackool | |
| 5,507,738 A | 4/1996 | Ciervo | |
| 5,527,331 A | 6/1996 | Kresch et al. | |
| 5,562,609 A | 10/1996 | Brumbach | |
| 5,562,610 A | 10/1996 | Brumbach | |
| 5,601,601 A | 2/1997 | Tal et al. | |
| 5,603,773 A | 2/1997 | Campbell | |
| 5,607,436 A | 3/1997 | Pratt et al. | |
| 5,618,492 A | 4/1997 | Auten et al. | |
| 5,628,760 A | 5/1997 | Knoepfler | |
| 5,630,420 A | 5/1997 | Vaitekunas | |
| D381,077 S | 7/1997 | Hunt | |
| 5,651,780 A | 7/1997 | Jackson et al. | |
| 5,653,713 A | 8/1997 | Michelson | |
| 5,669,922 A | 9/1997 | Hood | |
| 5,674,235 A | 10/1997 | Parisi | |
| 5,690,269 A | 11/1997 | Bolanos et al. | |
| 5,694,936 A | 12/1997 | Fujimoto et al. | |
| 5,713,896 A | 2/1998 | Nardella | |
| 5,730,752 A | 3/1998 | Alden et al. | |
| 5,733,074 A | 3/1998 | Stöck et al. | |
| 5,741,226 A | 4/1998 | Strukel et al. | |
| 5,792,135 A | 8/1998 | Madhani et al. | |
| 5,808,396 A | 9/1998 | Boukhny | |
| 5,810,859 A | 9/1998 | DiMatteo et al. | |
| 5,817,084 A | 10/1998 | Jensen | |
| 5,817,119 A | 10/1998 | Klieman et al. | |
| 5,827,323 A | 10/1998 | Klieman et al. | |
| 5,828,160 A | 10/1998 | Sugishita | |
| 5,836,897 A | 11/1998 | Sakurai et al. | |
| 5,843,109 A | 12/1998 | Mehta et al. | |
| 5,878,193 A | 3/1999 | Wang et al. | |
| 5,879,364 A | 3/1999 | Bromfield et al. | |
| 5,883,615 A | 3/1999 | Fago et al. | |
| 5,893,835 A | 4/1999 | Witt et al. | |
| 5,897,523 A | 4/1999 | Wright et al. | |
| 5,897,569 A | 4/1999 | Kellogg et al. | |
| 5,906,628 A | 5/1999 | Miyawaki et al. | |
| 5,935,143 A | 8/1999 | Hood | |
| 5,935,144 A | 8/1999 | Estabrook | |
| 5,938,633 A | 8/1999 | Beaupre | |
| 5,944,718 A | 8/1999 | Austin et al. | |
| 5,944,737 A | 8/1999 | Tsonton et al. | |
| 5,954,736 A | 9/1999 | Bishop et al. | |
| 5,954,746 A | 9/1999 | Holthaus et al. | |
| 5,957,882 A | 9/1999 | Nita et al. | |
| 5,957,943 A | 9/1999 | Vaitekunas | |
| 5,968,007 A | 10/1999 | Simon et al. | |
| 5,968,060 A | 10/1999 | Kellogg | |
| D416,089 S | 11/1999 | Barton et al. | |
| 5,980,510 A | 11/1999 | Tsonton et al. | |
| 5,989,274 A | 11/1999 | Davison et al. | |
| 5,989,275 A | 11/1999 | Estabrook et al. | |
| 5,993,972 A | 11/1999 | Reich et al. | |
| 6,024,741 A | 2/2000 | Williamson, IV et al. | |
| 6,027,515 A | 2/2000 | Cimino | |
| 6,033,375 A * | 3/2000 | Brumbach | 604/22 |
| 6,050,943 A | 4/2000 | Slayton et al. | |
| 6,051,010 A | 4/2000 | DiMatteo et al. | |
| 6,056,735 A | 5/2000 | Okada et al. | |
| 6,063,098 A | 5/2000 | Houser et al. | |
| 6,066,132 A | 5/2000 | Chen et al. | |
| 6,068,647 A | 5/2000 | Witt et al. | |

(56) References Cited

U.S. PATENT DOCUMENTS

| | | |
|---|---|---|
| 6,077,285 A | 6/2000 | Boukhny |
| 6,083,191 A | 7/2000 | Rose |
| 6,086,584 A | 7/2000 | Miller |
| 6,090,120 A | 7/2000 | Wright et al. |
| 6,109,500 A | 8/2000 | Alli et al. |
| 6,110,127 A | 8/2000 | Suzuki |
| 6,113,594 A | 9/2000 | Savage |
| 6,117,152 A | 9/2000 | Huitema |
| 6,126,629 A | 10/2000 | Perkins |
| 6,129,735 A | 10/2000 | Okada et al. |
| 6,132,368 A | 10/2000 | Cooper |
| 6,139,320 A | 10/2000 | Hahn |
| 6,139,561 A | 10/2000 | Shibata et al. |
| 6,142,615 A | 11/2000 | Qiu et al. |
| 6,147,560 A | 11/2000 | Erhage et al. |
| 6,152,902 A | 11/2000 | Christian et al. |
| 6,159,160 A | 12/2000 | Hsei et al. |
| 6,159,175 A | 12/2000 | Strukel et al. |
| 6,165,150 A | 12/2000 | Banko |
| 6,204,592 B1 | 3/2001 | Hur |
| 6,206,844 B1 | 3/2001 | Reichel et al. |
| 6,210,403 B1 | 4/2001 | Klicek |
| 6,214,023 B1 | 4/2001 | Whipple et al. |
| 6,231,565 B1 | 5/2001 | Tovey et al. |
| 6,233,476 B1 | 5/2001 | Strommer et al. |
| 6,238,366 B1 | 5/2001 | Savage et al. |
| 6,252,110 B1 | 6/2001 | Uemura et al. |
| D444,365 S | 7/2001 | Bass et al. |
| 6,254,623 B1 | 7/2001 | Haibel, Jr. et al. |
| 6,258,034 B1 | 7/2001 | Hanafy |
| 6,267,761 B1 | 7/2001 | Ryan |
| 6,270,831 B2 | 8/2001 | Kumar et al. |
| 6,273,852 B1 | 8/2001 | Lehe et al. |
| 6,274,963 B1 | 8/2001 | Estabrook et al. |
| 6,277,115 B1 | 8/2001 | Saadat |
| 6,278,218 B1 | 8/2001 | Madan et al. |
| 6,283,981 B1 | 9/2001 | Beaupre |
| 6,309,400 B2 | 10/2001 | Beaupre |
| 6,319,221 B1 | 11/2001 | Savage et al. |
| 6,325,811 B1 | 12/2001 | Messerly |
| 6,328,751 B1 | 12/2001 | Beaupre |
| 6,340,352 B1 | 1/2002 | Okada et al. |
| 6,352,532 B1 | 3/2002 | Kramer et al. |
| 6,364,888 B1 | 4/2002 | Niemeyer et al. |
| 6,379,320 B1 | 4/2002 | Lafon et al. |
| D457,958 S | 5/2002 | Dycus et al. |
| 6,383,194 B1 | 5/2002 | Pothula |
| 6,387,109 B1 | 5/2002 | Davison et al. |
| 6,388,657 B1 | 5/2002 | Natoli |
| 6,391,042 B1 | 5/2002 | Cimino |
| 6,405,733 B1 | 6/2002 | Fogarty et al. |
| 6,416,486 B1 | 7/2002 | Wampler |
| 6,423,073 B2 | 7/2002 | Bowman |
| 6,423,082 B1 | 7/2002 | Houser et al. |
| 6,428,539 B1 | 8/2002 | Baxter et al. |
| 6,432,118 B1 | 8/2002 | Messerly |
| 6,436,114 B1 | 8/2002 | Novak et al. |
| 6,436,115 B1 | 8/2002 | Beaupre |
| 6,443,969 B1 | 9/2002 | Novak et al. |
| 6,454,781 B1 | 9/2002 | Witt et al. |
| 6,454,782 B1 | 9/2002 | Schwemberger |
| 6,458,142 B1 | 10/2002 | Faller et al. |
| 6,480,796 B2 | 11/2002 | Wiener |
| 6,485,490 B2 | 11/2002 | Wampler et al. |
| 6,491,708 B2 | 12/2002 | Madan et al. |
| 6,497,715 B2 | 12/2002 | Satou |
| 6,500,176 B1 | 12/2002 | Truckai et al. |
| 6,500,188 B2 | 12/2002 | Harper et al. |
| 6,524,251 B2 | 2/2003 | Rabiner et al. |
| 6,524,316 B1 | 2/2003 | Nicholson et al. |
| 6,527,736 B1 | 3/2003 | Attinger et al. |
| 6,533,784 B2 | 3/2003 | Truckai et al. |
| 6,537,291 B2 | 3/2003 | Friedman et al. |
| 6,543,452 B1 * | 4/2003 | Lavigne .................. 128/207.18 |
| 6,543,456 B1 | 4/2003 | Freeman |
| 6,544,260 B1 | 4/2003 | Markel et al. |
| 6,561,983 B2 | 5/2003 | Cronin et al. |
| 6,572,632 B2 | 6/2003 | Zisterer et al. |
| 6,575,969 B1 | 6/2003 | Rittman, III et al. |
| 6,582,451 B1 | 6/2003 | Marucci et al. |
| 6,589,200 B1 | 7/2003 | Schwemberger et al. |
| 6,589,239 B2 | 7/2003 | Khandkar et al. |
| 6,610,059 B1 | 8/2003 | West, Jr. |
| 6,616,450 B2 | 9/2003 | Mossle et al. |
| 6,623,501 B2 | 9/2003 | Heller et al. |
| 6,626,926 B2 | 9/2003 | Friedman et al. |
| 6,633,234 B2 | 10/2003 | Wiener et al. |
| 6,656,177 B2 | 12/2003 | Truckai et al. |
| 6,662,127 B2 | 12/2003 | Wiener et al. |
| 6,663,941 B2 | 12/2003 | Brown et al. |
| 6,669,690 B1 | 12/2003 | Okada et al. |
| 6,676,660 B2 | 1/2004 | Wampler et al. |
| 6,678,621 B2 | 1/2004 | Wiener et al. |
| 6,679,899 B2 | 1/2004 | Wiener et al. |
| 6,682,544 B2 | 1/2004 | Mastri et al. |
| 6,689,146 B1 | 2/2004 | Himes |
| 6,716,215 B1 | 4/2004 | David et al. |
| 6,731,047 B2 | 5/2004 | Kauf et al. |
| 6,733,506 B1 | 5/2004 | McDevitt et al. |
| 6,762,535 B2 | 7/2004 | Take et al. |
| 6,770,072 B1 | 8/2004 | Truckai et al. |
| 6,773,443 B2 | 8/2004 | Truwit et al. |
| 6,773,444 B2 | 8/2004 | Messerly |
| 6,783,524 B2 | 8/2004 | Anderson et al. |
| 6,786,382 B1 | 9/2004 | Hoffman |
| 6,786,383 B2 | 9/2004 | Stegelmann |
| 6,790,216 B1 | 9/2004 | Ishikawa |
| 6,802,843 B2 | 10/2004 | Truckai et al. |
| 6,827,712 B2 | 12/2004 | Tovey et al. |
| 6,828,712 B2 | 12/2004 | Battaglin et al. |
| 6,869,439 B2 | 3/2005 | White et al. |
| 6,875,220 B2 | 4/2005 | Du et al. |
| 6,905,497 B2 | 6/2005 | Truckai et al. |
| 6,908,472 B2 | 6/2005 | Wiener et al. |
| 6,913,579 B2 | 7/2005 | Truckai et al. |
| 6,923,804 B2 | 8/2005 | Eggers et al. |
| 6,926,716 B2 | 8/2005 | Baker et al. |
| 6,929,632 B2 | 8/2005 | Nita et al. |
| 6,929,644 B2 | 8/2005 | Truckai et al. |
| 6,933,656 B2 | 8/2005 | Matsushita et al. |
| D509,589 S | 9/2005 | Wells |
| 6,942,677 B2 | 9/2005 | Nita et al. |
| 6,945,981 B2 | 9/2005 | Donofrio et al. |
| D511,145 S | 11/2005 | Donofrio et al. |
| 6,976,844 B2 | 12/2005 | Hickok et al. |
| 6,976,969 B2 | 12/2005 | Messerly |
| 6,977,495 B2 | 12/2005 | Donofrio |
| 6,984,220 B2 | 1/2006 | Wuchinich |
| 7,001,335 B2 | 2/2006 | Adachi et al. |
| 7,011,657 B2 | 3/2006 | Truckai et al. |
| 7,033,357 B2 | 4/2006 | Baxter et al. |
| 7,041,083 B2 | 5/2006 | Chu et al. |
| 7,041,088 B2 | 5/2006 | Nawrocki et al. |
| 7,041,102 B2 | 5/2006 | Truckai et al. |
| 7,070,597 B2 | 7/2006 | Truckai et al. |
| 7,074,219 B2 | 7/2006 | Levine et al. |
| 7,077,039 B2 | 7/2006 | Gass et al. |
| 7,077,853 B2 | 7/2006 | Kramer et al. |
| 7,083,619 B2 | 8/2006 | Truckai et al. |
| 7,087,054 B2 | 8/2006 | Truckai et al. |
| 7,090,672 B2 | 8/2006 | Underwood et al. |
| 7,101,378 B2 | 9/2006 | Salameh et al. |
| 7,108,695 B2 | 9/2006 | Witt et al. |
| 7,112,201 B2 | 9/2006 | Truckai et al. |
| 7,118,564 B2 | 10/2006 | Ritchie et al. |
| 7,124,932 B2 | 10/2006 | Isaacson et al. |
| 7,125,409 B2 | 10/2006 | Truckai et al. |
| 7,135,018 B2 | 11/2006 | Ryan et al. |
| 7,135,030 B2 | 11/2006 | Schwemberger et al. |
| 7,144,403 B2 | 12/2006 | Booth |
| 7,153,315 B2 | 12/2006 | Miller |
| D536,093 S | 1/2007 | Nakajima et al. |
| 7,156,189 B1 | 1/2007 | Bar-Cohen et al. |
| 7,156,853 B2 | 1/2007 | Muratsu |

(56) References Cited

U.S. PATENT DOCUMENTS

| | | | |
|---|---|---|---|
| 7,157,058 B2 | 1/2007 | Marhasin et al. |
| 7,159,750 B2 | 1/2007 | Racenet et al. |
| 7,163,548 B2 | 1/2007 | Stulen et al. |
| 7,169,146 B2 | 1/2007 | Truckai et al. |
| 7,179,271 B2 | 2/2007 | Friedman et al. |
| 7,186,253 B2 | 3/2007 | Truckai et al. |
| 7,189,233 B2 | 3/2007 | Truckai et al. |
| 7,204,820 B2 | 4/2007 | Akahoshi |
| 7,217,269 B2 | 5/2007 | El-Galley et al. |
| 7,220,951 B2 | 5/2007 | Truckai et al. |
| 7,223,229 B2 | 5/2007 | Inman et al. |
| 7,229,455 B2 | 6/2007 | Sakurai et al. |
| 7,273,483 B2 | 9/2007 | Wiener et al. |
| 7,285,895 B2 | 10/2007 | Beaupré |
| 7,309,849 B2 | 12/2007 | Truckai et al. |
| 7,311,709 B2 | 12/2007 | Truckai et al. |
| 7,317,955 B2 | 1/2008 | McGreevy |
| 7,326,236 B2 | 2/2008 | Andreas et al. |
| 7,331,410 B2 | 2/2008 | Yong et al. |
| 7,353,068 B2 | 4/2008 | Tanaka et al. |
| 7,354,440 B2 | 4/2008 | Truckai et al. |
| 7,380,695 B2 | 6/2008 | Doll et al. |
| 7,380,696 B2 | 6/2008 | Shelton, IV et al. |
| 7,381,209 B2 | 6/2008 | Truckai et al. |
| 7,390,317 B2 | 6/2008 | Taylor et al. |
| 7,404,508 B2 | 7/2008 | Smith et al. |
| 7,408,288 B2 | 8/2008 | Hara |
| D576,725 S | 9/2008 | Shumer et al. |
| D578,643 S | 10/2008 | Shumer et al. |
| D578,644 S | 10/2008 | Shumer et al. |
| D578,645 S | 10/2008 | Shumer et al. |
| 7,431,704 B2 | 10/2008 | Babaev |
| 7,441,684 B2 | 10/2008 | Shelton, IV et al. |
| 7,455,208 B2 | 11/2008 | Wales et al. |
| 7,472,815 B2 | 1/2009 | Shelton, IV et al. |
| 7,473,263 B2 | 1/2009 | Johnston et al. |
| 7,479,148 B2 | 1/2009 | Beaupre |
| 7,479,160 B2 | 1/2009 | Branch et al. |
| 7,494,468 B2 | 2/2009 | Rabiner et al. |
| 7,503,893 B2 | 3/2009 | Kucklick |
| 7,503,895 B2 | 3/2009 | Rabiner et al. |
| 7,506,790 B2 | 3/2009 | Shelton, IV |
| 7,506,791 B2 | 3/2009 | Omaits et al. |
| 7,524,320 B2 | 4/2009 | Tierney et al. |
| 7,534,243 B1 | 5/2009 | Chin et al. |
| D594,983 S | 6/2009 | Price et al. |
| 7,549,564 B2 | 6/2009 | Boudreaux |
| 7,559,450 B2 | 7/2009 | Wales et al. |
| 7,567,012 B2 | 7/2009 | Namikawa |
| 7,578,820 B2 | 8/2009 | Moore et al. |
| 7,654,431 B2 | 2/2010 | Hueil et al. |
| 7,665,647 B2 | 2/2010 | Shelton, IV et al. |
| 7,670,334 B2 | 3/2010 | Hueil et al. |
| 7,674,263 B2 | 3/2010 | Ryan |
| 7,691,098 B2 | 4/2010 | Wallace et al. |
| 7,713,202 B2 | 5/2010 | Boukhny et al. |
| 7,714,481 B2 | 5/2010 | Sakai |
| D618,797 S | 6/2010 | Price et al. |
| 7,751,115 B2 | 7/2010 | Song |
| 7,770,774 B2 | 8/2010 | Mastri et al. |
| 7,770,775 B2 | 8/2010 | Shelton, IV et al. |
| 7,780,054 B2 | 8/2010 | Wales |
| 7,780,659 B2 | 8/2010 | Okada et al. |
| 7,784,662 B2 | 8/2010 | Wales et al. |
| 7,798,386 B2 | 9/2010 | Schall et al. |
| 7,806,891 B2 | 10/2010 | Nowlin et al. |
| 7,810,693 B2 | 10/2010 | Broehl et al. |
| 7,824,401 B2 | 11/2010 | Manzo et al. |
| 7,837,699 B2 | 11/2010 | Yamada et al. |
| 7,854,735 B2 | 12/2010 | Houser et al. |
| D631,155 S | 1/2011 | Peine et al. |
| 7,861,906 B2 | 1/2011 | Doll et al. |
| 7,876,030 B2 | 1/2011 | Taki et al. |
| D631,965 S | 2/2011 | Price et al. |
| 7,892,606 B2 | 2/2011 | Thies et al. |
| 7,901,423 B2 | 3/2011 | Stulen et al. |
| 7,905,881 B2 | 3/2011 | Masuda et al. |
| 7,922,651 B2 | 4/2011 | Yamada et al. |
| 7,959,050 B2 | 6/2011 | Smith et al. |
| 7,959,626 B2 | 6/2011 | Hong et al. |
| 7,976,544 B2 | 7/2011 | McClurken et al. |
| 7,998,157 B2 | 8/2011 | Culp et al. |
| 8,038,693 B2 | 10/2011 | Allen |
| 8,061,014 B2 | 11/2011 | Smith et al. |
| 8,089,197 B2 | 1/2012 | Rinner et al. |
| 8,152,825 B2 | 4/2012 | Madan et al. |
| 8,157,145 B2 | 4/2012 | Shelton, IV et al. |
| 8,177,800 B2 | 5/2012 | Spitz et al. |
| D661,801 S | 6/2012 | Price et al. |
| D661,802 S | 6/2012 | Price et al. |
| D661,803 S | 6/2012 | Price et al. |
| D661,804 S | 6/2012 | Price et al. |
| 8,197,502 B2 | 6/2012 | Smith et al. |
| 8,236,020 B2 | 8/2012 | Smith et al. |
| 8,253,303 B2 | 8/2012 | Giordano et al. |
| 8,333,778 B2 | 12/2012 | Smith et al. |
| 8,333,779 B2 | 12/2012 | Smith et al. |
| 8,334,468 B2 | 12/2012 | Palmer et al. |
| 8,338,726 B2 | 12/2012 | Palmer et al. |
| 8,372,101 B2 | 2/2013 | Smith et al. |
| 8,377,059 B2 | 2/2013 | Deville et al. |
| 8,377,085 B2 | 2/2013 | Smith et al. |
| 8,418,349 B2 | 4/2013 | Smith et al. |
| 8,439,939 B2 | 5/2013 | Deville et al. |
| 8,479,969 B2 | 7/2013 | Shelton, IV |
| 8,491,578 B2 | 7/2013 | Manwaring et al. |
| 8,535,340 B2 | 9/2013 | Allen |
| 8,535,341 B2 | 9/2013 | Allen |
| 8,546,996 B2 | 10/2013 | Messerly et al. |
| 8,546,999 B2 | 10/2013 | Houser et al. |
| 8,573,461 B2 | 11/2013 | Shelton, IV et al. |
| 8,573,465 B2 | 11/2013 | Shelton, IV |
| 8,602,288 B2 | 12/2013 | Shelton, IV et al. |
| 8,616,431 B2 | 12/2013 | Timm et al. |
| 8,709,031 B2 | 4/2014 | Stulen |
| 2001/0025183 A1 | 9/2001 | Shahidi |
| 2001/0025184 A1 | 9/2001 | Messerly |
| 2001/0031950 A1 | 10/2001 | Ryan |
| 2001/0039419 A1 | 11/2001 | Francischelli et al. |
| 2002/0002377 A1 | 1/2002 | Cimino |
| 2002/0019649 A1 | 2/2002 | Sikora et al. |
| 2002/0022836 A1 | 2/2002 | Goble et al. |
| 2002/0049551 A1 | 4/2002 | Friedman et al. |
| 2002/0052617 A1 | 5/2002 | Anis et al. |
| 2002/0077550 A1 | 6/2002 | Rabiner et al. |
| 2002/0156493 A1 | 10/2002 | Houser et al. |
| 2003/0036705 A1 | 2/2003 | Hare et al. |
| 2003/0055443 A1 | 3/2003 | Spotnitz |
| 2003/0204199 A1 | 10/2003 | Novak et al. |
| 2003/0212332 A1 | 11/2003 | Fenton et al. |
| 2003/0212422 A1 | 11/2003 | Fenton et al. |
| 2003/0229344 A1 | 12/2003 | Dycus et al. |
| 2004/0030254 A1 | 2/2004 | Babaev |
| 2004/0047485 A1 | 3/2004 | Sherrit et al. |
| 2004/0054364 A1 | 3/2004 | Aranyi et al. |
| 2004/0092921 A1 | 5/2004 | Kadziauskas et al. |
| 2004/0097919 A1 | 5/2004 | Wellman et al. |
| 2004/0097996 A1 | 5/2004 | Rabiner et al. |
| 2004/0199193 A1 | 10/2004 | Hayashi et al. |
| 2004/0204728 A1 | 10/2004 | Haefner |
| 2004/0243157 A1* | 12/2004 | Connor et al. ............... 606/159 |
| 2004/0260300 A1 | 12/2004 | Gorensek et al. |
| 2005/0021065 A1 | 1/2005 | Yamada et al. |
| 2005/0033337 A1 | 2/2005 | Muir et al. |
| 2005/0049546 A1 | 3/2005 | Messerly et al. |
| 2005/0070800 A1 | 3/2005 | Takahashi |
| 2005/0096683 A1 | 5/2005 | Ellins et al. |
| 2005/0143769 A1 | 6/2005 | White et al. |
| 2005/0149108 A1 | 7/2005 | Cox |
| 2005/0165345 A1 | 7/2005 | Laufer et al. |
| 2005/0177184 A1 | 8/2005 | Easley |
| 2005/0192610 A1 | 9/2005 | Houser et al. |
| 2005/0209620 A1 | 9/2005 | Du et al. |
| 2005/0261581 A1 | 11/2005 | Hughes et al. |

(56) References Cited

U.S. PATENT DOCUMENTS

| | | |
|---|---|---|
| 2005/0261588 A1 | 11/2005 | Makin et al. |
| 2005/0273090 A1 | 12/2005 | Nieman et al. |
| 2005/0288659 A1 | 12/2005 | Kimura et al. |
| 2006/0030797 A1 | 2/2006 | Zhou et al. |
| 2006/0063130 A1 | 3/2006 | Hayman et al. |
| 2006/0066181 A1 | 3/2006 | Bromfield et al. |
| 2006/0079878 A1 | 4/2006 | Houser |
| 2006/0084963 A1 | 4/2006 | Messerly |
| 2006/0095046 A1 | 5/2006 | Trieu et al. |
| 2006/0190034 A1 | 8/2006 | Nishizawa et al. |
| 2006/0206115 A1 | 9/2006 | Schomer et al. |
| 2006/0211943 A1 | 9/2006 | Beaupre |
| 2006/0235306 A1 | 10/2006 | Cotter et al. |
| 2006/0253050 A1 | 11/2006 | Yoshimine et al. |
| 2006/0264809 A1 | 11/2006 | Hansmann et al. |
| 2007/0016235 A1 | 1/2007 | Tanaka et al. |
| 2007/0016236 A1 | 1/2007 | Beaupre |
| 2007/0055228 A1 | 3/2007 | Berg et al. |
| 2007/0056596 A1 | 3/2007 | Fanney et al. |
| 2007/0060915 A1 | 3/2007 | Kucklick |
| 2007/0060935 A1 | 3/2007 | Schwardt et al. |
| 2007/0063618 A1 | 3/2007 | Bromfield |
| 2007/0106317 A1 | 5/2007 | Shelton et al. |
| 2007/0129716 A1 | 6/2007 | Daw et al. |
| 2007/0130771 A1 | 6/2007 | Ehlert et al. |
| 2007/0131034 A1 | 6/2007 | Ehlert et al. |
| 2007/0149881 A1 | 6/2007 | Rabin |
| 2007/0162050 A1 | 7/2007 | Sartor |
| 2007/0173872 A1 | 7/2007 | Neuenfeldt |
| 2007/0185380 A1 | 8/2007 | Kucklick |
| 2007/0219481 A1 | 9/2007 | Babaev |
| 2007/0239028 A1* | 10/2007 | Houser et al. .................. 600/471 |
| 2007/0249941 A1 | 10/2007 | Salehi et al. |
| 2007/0260234 A1 | 11/2007 | McCullagh et al. |
| 2007/0265560 A1 | 11/2007 | Soltani et al. |
| 2007/0275348 A1 | 11/2007 | Lemon |
| 2007/0282335 A1 | 12/2007 | Young et al. |
| 2007/0287933 A1 | 12/2007 | Phan et al. |
| 2008/0009848 A1 | 1/2008 | Paraschiv et al. |
| 2008/0051812 A1 | 2/2008 | Schmitz et al. |
| 2008/0058585 A1 | 3/2008 | Novak et al. |
| 2008/0058775 A1 | 3/2008 | Darian et al. |
| 2008/0058845 A1 | 3/2008 | Shimizu et al. |
| 2008/0082039 A1 | 4/2008 | Babaev |
| 2008/0082098 A1 | 4/2008 | Tanaka et al. |
| 2008/0171938 A1 | 7/2008 | Masuda et al. |
| 2008/0172051 A1 | 7/2008 | Masuda et al. |
| 2008/0177268 A1 | 7/2008 | Daum et al. |
| 2008/0188878 A1 | 8/2008 | Young |
| 2008/0200940 A1 | 8/2008 | Eichmann et al. |
| 2008/0208231 A1 | 8/2008 | Ota et al. |
| 2008/0234708 A1 | 9/2008 | Houser et al. |
| 2008/0234709 A1 | 9/2008 | Houser |
| 2008/0234710 A1 | 9/2008 | Neurohr et al. |
| 2008/0234711 A1 | 9/2008 | Houser et al. |
| 2008/0243106 A1 | 10/2008 | Coe et al. |
| 2008/0245371 A1 | 10/2008 | Gruber |
| 2008/0249553 A1 | 10/2008 | Gruber et al. |
| 2008/0262490 A1 | 10/2008 | Williams |
| 2008/0281200 A1 | 11/2008 | Voic et al. |
| 2008/0287948 A1 | 11/2008 | Newton et al. |
| 2009/0030311 A1 | 1/2009 | Stulen et al. |
| 2009/0030351 A1 | 1/2009 | Wiener et al. |
| 2009/0030437 A1 | 1/2009 | Houser et al. |
| 2009/0030438 A1 | 1/2009 | Stulen |
| 2009/0030439 A1 | 1/2009 | Stulen |
| 2009/0036911 A1 | 2/2009 | Stulen |
| 2009/0036912 A1 | 2/2009 | Wiener et al. |
| 2009/0036913 A1 | 2/2009 | Wiener et al. |
| 2009/0036914 A1 | 2/2009 | Houser |
| 2009/0048537 A1 | 2/2009 | Lydon et al. |
| 2009/0054886 A1 | 2/2009 | Yachi et al. |
| 2009/0054894 A1 | 2/2009 | Yachi |
| 2009/0076506 A1 | 3/2009 | Baker |
| 2009/0082716 A1 | 3/2009 | Akahoshi |
| 2009/0105750 A1 | 4/2009 | Price et al. |
| 2009/0118802 A1 | 5/2009 | Mioduski et al. |
| 2009/0138006 A1 | 5/2009 | Bales et al. |
| 2009/0143795 A1 | 6/2009 | Robertson |
| 2009/0143797 A1 | 6/2009 | Smith et al. |
| 2009/0143798 A1 | 6/2009 | Smith et al. |
| 2009/0143799 A1 | 6/2009 | Smith et al. |
| 2009/0143800 A1 | 6/2009 | Deville et al. |
| 2009/0143801 A1 | 6/2009 | Deville et al. |
| 2009/0143802 A1 | 6/2009 | Deville et al. |
| 2009/0143803 A1 | 6/2009 | Palmer et al. |
| 2009/0143804 A1 | 6/2009 | Palmer et al. |
| 2009/0143805 A1 | 6/2009 | Palmer et al. |
| 2009/0143806 A1 | 6/2009 | Witt et al. |
| 2009/0149801 A1 | 6/2009 | Crandall et al. |
| 2009/0270853 A1 | 10/2009 | Yachi et al. |
| 2009/0270899 A1 | 10/2009 | Carusillo et al. |
| 2009/0318945 A1 | 12/2009 | Yoshimine et al. |
| 2009/0327715 A1 | 12/2009 | Smith et al. |
| 2010/0004668 A1 | 1/2010 | Smith et al. |
| 2010/0004669 A1 | 1/2010 | Smith et al. |
| 2010/0016785 A1 | 1/2010 | Takuma |
| 2010/0030248 A1 | 2/2010 | Palmer et al. |
| 2010/0036370 A1 | 2/2010 | Mirel et al. |
| 2010/0036405 A1 | 2/2010 | Giordano et al. |
| 2010/0069940 A1 | 3/2010 | Miller et al. |
| 2010/0158307 A1 | 6/2010 | Kubota et al. |
| 2010/0179577 A1 | 7/2010 | Houser |
| 2010/0187283 A1 | 7/2010 | Crainich et al. |
| 2010/0193567 A1 | 8/2010 | Scheib et al. |
| 2010/0234906 A1 | 9/2010 | Koh |
| 2010/0298743 A1 | 11/2010 | Nield et al. |
| 2010/0298851 A1 | 11/2010 | Nield |
| 2010/0331869 A1 | 12/2010 | Voegele et al. |
| 2010/0331870 A1 | 12/2010 | Wan et al. |
| 2010/0331871 A1 | 12/2010 | Nield et al. |
| 2010/0331872 A1 | 12/2010 | Houser et al. |
| 2011/0009850 A1 | 1/2011 | Main et al. |
| 2011/0015627 A1 | 1/2011 | Dinardo et al. |
| 2011/0015631 A1 | 1/2011 | Wiener et al. |
| 2011/0015660 A1 | 1/2011 | Wiener et al. |
| 2011/0082486 A1 | 4/2011 | Messerly et al. |
| 2011/0087212 A1 | 4/2011 | Aldridge et al. |
| 2011/0087213 A1 | 4/2011 | Messerly et al. |
| 2011/0087214 A1 | 4/2011 | Giordano et al. |
| 2011/0087215 A1 | 4/2011 | Aldridge et al. |
| 2011/0087216 A1 | 4/2011 | Aldridge et al. |
| 2011/0087217 A1 | 4/2011 | Yates et al. |
| 2011/0087218 A1 | 4/2011 | Boudreaux et al. |
| 2011/0087256 A1 | 4/2011 | Wiener et al. |
| 2011/0125175 A1 | 5/2011 | Stulen et al. |
| 2011/0196286 A1 | 8/2011 | Robertson et al. |
| 2011/0196287 A1 | 8/2011 | Robertson et al. |
| 2011/0196398 A1 | 8/2011 | Robertson et al. |
| 2011/0196399 A1 | 8/2011 | Robertson et al. |
| 2011/0196400 A1 | 8/2011 | Robertson et al. |
| 2011/0196401 A1 | 8/2011 | Robertson et al. |
| 2011/0196402 A1 | 8/2011 | Robertson et al. |
| 2011/0196403 A1 | 8/2011 | Robertson et al. |
| 2011/0196405 A1 | 8/2011 | Dietz |
| 2011/0288452 A1 | 11/2011 | Houser et al. |
| 2012/0029546 A1 | 2/2012 | Robertson |
| 2012/0059289 A1 | 3/2012 | Nield et al. |
| 2012/0078139 A1 | 3/2012 | Aldridge et al. |
| 2012/0078247 A1 | 3/2012 | Worrell et al. |
| 2012/0083783 A1 | 4/2012 | Davison et al. |
| 2012/0083784 A1 | 4/2012 | Davison et al. |
| 2012/0138660 A1 | 6/2012 | Shelton, IV |
| 2012/0177005 A1 | 7/2012 | Liang et al. |
| 2012/0184946 A1 | 7/2012 | Price et al. |
| 2012/0199630 A1 | 8/2012 | Shelton, IV |
| 2012/0199632 A1 | 8/2012 | Spivey et al. |
| 2012/0203247 A1 | 8/2012 | Shelton, IV et al. |
| 2012/0203257 A1 | 8/2012 | Stulen et al. |
| 2012/0210223 A1 | 8/2012 | Eppolito |
| 2012/0259353 A1 | 10/2012 | Houser et al. |
| 2012/0265196 A1 | 10/2012 | Turner et al. |
| 2012/0269676 A1 | 10/2012 | Houser et al. |
| 2012/0310262 A1 | 12/2012 | Messerly et al. |

(56) References Cited

U.S. PATENT DOCUMENTS

| | | |
|---|---|---|
| 2012/0310264 A1 | 12/2012 | Messerly et al. |
| 2013/0012970 A1 | 1/2013 | Houser |
| 2013/0245659 A1 | 9/2013 | Robertson et al. |

FOREIGN PATENT DOCUMENTS

| | | |
|---|---|---|
| CN | 1694649 A | 11/2005 |
| CN | 1922563 A | 2/2007 |
| CN | 101040799 A | 9/2007 |
| EP | 0171967 A2 | 2/1986 |
| EP | 0443256 A1 | 8/1991 |
| EP | 0456470 A1 | 11/1991 |
| EP | 0482195 B1 | 4/1992 |
| EP | 0482195 81 | 1/1996 |
| EP | 0612570 B1 | 6/1997 |
| EP | 0908148 B1 | 1/2002 |
| EP | 0908155 B1 | 6/2003 |
| EP | 1199044 B1 | 12/2005 |
| EP | 1433425 B1 | 6/2006 |
| EP | 1844720 A1 | 10/2007 |
| EP | 1862133 A1 | 12/2007 |
| EP | 1974771 A1 | 10/2008 |
| EP | 1832259 B1 | 6/2009 |
| EP | 2074959 A1 | 7/2009 |
| GB | 2032221 A | 4/1980 |
| GB | 2379878 B | 11/2004 |
| GB | 2447767 B | 8/2011 |
| JP | H 04-152942 A | 5/1992 |
| JP | 6-104503 A | 4/1994 |
| JP | 2005027026 A | 1/2005 |
| JP | 2005027026 A | 8/2006 |
| WO | WO 92/22259 A2 | 12/1992 |
| WO | WO 93/14708 A1 | 8/1993 |
| WO | WO 98/37815 A1 | 9/1998 |
| WO | WO 01/54590 A1 | 8/2001 |
| WO | WO 01/95810 A2 | 12/2001 |
| WO | WO 2004/037095 A2 | 5/2004 |
| WO | WO 2005/122917 A1 | 12/2005 |
| WO | WO 2006/042210 A2 | 4/2006 |
| WO | WO 2006/058223 A2 | 6/2006 |
| WO | WO 2006/129465 A1 | 12/2006 |
| WO | WO 2007/008710 A2 | 1/2007 |
| WO | WO 2007/047531 A2 | 4/2007 |
| WO | WO 2007/143665 A2 | 12/2007 |
| WO | WO 2008/016886 A2 | 2/2008 |
| WO | WO 2008/130793 A1 | 10/2008 |
| WO | WO 2009/018406 A2 | 2/2009 |
| WO | WO 2009/027065 A1 | 3/2009 |
| WO | WO 2011/144911 A1 | 11/2011 |

OTHER PUBLICATIONS

Sherrit et al., "Novel Horn Designs for Ultrasonic/Sonic Cleaning Welding, Soldering, Cutting and Drilling," Proc. SPIE Smart Structures Conference, vol. 4701, Paper No. 34, San Diego, CA, pp. 353-360, Mar. 2002.

AST Products, Inc., "Principles of Video Contact Angle Analysis," 20 pages, (2006).

Lim et al., "A Review of Mechanism Used in Laparoscopic Surgical Instruments," Mechanism and Machine Theory, vol. 38, pp. 1133-1147, (2003).

Gooch et al., "Recommended Infection-Control Practices for Dentistry, 1993," Published: May 28, 1993; [retrieved on Aug. 23, 2008]. Retrieved from the internet: URL: http//wonder.cdc.gov/wonder/prevguid/p0000191/p0000191.asp (15 pages).

Huston et al., "Magnetic and Magnetostrictive Properties of Cube Textured Nickel for Magnetostrictive Transducer Applications," IEEE Transactions on Magnetics, vol. 9(4), pp. 636-640 (Dec. 1973).

U.S. Appl. No. 12/896,351, filed Oct. 1, 2010.
U.S. Appl. No. 12/896,479, filed Oct. 1, 2010.
U.S. Appl. No. 12/896,360, filed Oct. 1, 2010.
U.S. Appl. No. 12/896,345, filed Oct. 1, 2010.
U.S. Appl. No. 12/896,384, filed Oct. 1, 2010.
U.S. Appl. No. 12/896,467, filed Oct. 1, 2010.
U.S. Appl. No. 12/896,451, filed Oct. 1, 2010.
U.S. Appl. No. 12/896,470, filed Oct. 1, 2010.
U.S. Appl. No. 12/896,411, filed Oct. 1, 2010.
U.S. Appl. No. 12/896,420, filed Oct. 1, 2010.
U.S. Appl. No. 12/703,860, filed Feb. 11, 2010.
U.S. Appl. No. 12/703,864, filed Feb. 11, 2010.
U.S. Appl. No. 12/703,866, filed Feb. 11, 2010.
U.S. Appl. No. 12/703,870, filed Feb. 11, 2010.
U.S. Appl. No. 12/703,875, filed Feb. 11, 2010.
U.S. Appl. No. 12/703,877, filed Feb. 11, 2010.
U.S. Appl. No. 12/703,879, filed Feb. 11, 2010.
U.S. Appl. No. 12/703,885, filed Feb. 11, 2010.
U.S. Appl. No. 12/703,899, filed Feb. 11, 2010.

International Search Report for PCT/US2011/024180, Apr. 12, 2011 included in the PCT Publication for WO 2011/100313 A1 (73 pages).

Incropera et al., Fundamentals of Heat and Mass Transfer, Wiley, New York (1990). (Book—not attached).

F. A. Duck, "Optical Properties of Tissue Including Ultraviolet and Infrared Radiation," pp. 43-71 in *Physical Properties of Tissue* (1990).

Orr et al., "Overview of Bioheat Transfer," pp. 367-384 in Optical-Thermal Response of Laser-Irradiated Tissue, A. J. Welch and M. J. C. van Gernert, eds., Plenum, New York (1995).

Campbell et al, "Thermal Imaging in Surgery," p. 19-3, in *Medical Infrared Imaging*, N. A. Diakides and J. D. Bronzino, Eds. (2008).

U.S. Appl. No. 29/402,697, filed Sep. 26, 2011.
U.S. Appl. No. 29/402,699, filed Sep. 26, 2011.
U.S. Appl. No. 29/402,700, filed Sep. 26, 2011.
U.S. Appl. No. 29/402,701, filed Sep. 26, 2011.
U.S. Appl. No. 29/404,676, filed Oct. 24, 2011.
U.S. Appl. No. 13/294,576, filed Nov. 11, 2011.
U.S. Appl. No. 13/448,175, filed Apr. 16, 2012.
U.S. Appl. No. 13/151,181, filed Jun. 2, 2011.
U.S. Appl. No. 13/369,561, filed Feb. 9, 2012.
U.S. Appl. No. 13/369,569, filed Feb. 9, 2012.
U.S. Appl. No. 13/369,578, filed Feb. 9, 2012.
U.S. Appl. No. 13/369,584, filed Feb. 9, 2012.
U.S. Appl. No. 13/369,588, filed Feb. 9, 2012.
U.S. Appl. No. 13/369,594, filed Feb. 9, 2012.
U.S. Appl. No. 13/369,601, filed Feb. 9, 2012.
U.S. Appl. No. 13/369,609, filed Feb. 9, 2012.
U.S. Appl. No. 13/369,629, filed Feb. 9, 2012.
U.S. Appl. No. 13/369,666, filed Feb. 9, 2012.
U.S. Appl. No. 13/545,292, filed Jul. 10, 2012.
U.S. Appl. No. 13/584,020, filed Aug. 13, 2012.
U.S. Appl. No. 13/584,445, filed Aug. 13, 2012.
U.S. Appl. No. 13/584,878, filed Aug. 14, 2012.
U.S. Appl. No. 13/585,124, filed Aug. 14, 2012.
U.S. Appl. No. 13/585,292, filed Aug. 14, 2012.
U.S. Appl. No. 13/942,103, filed Jul. 15, 2013.
U.S. Appl. No. 13/751,680, filed Jan. 28, 2013.

\* cited by examiner

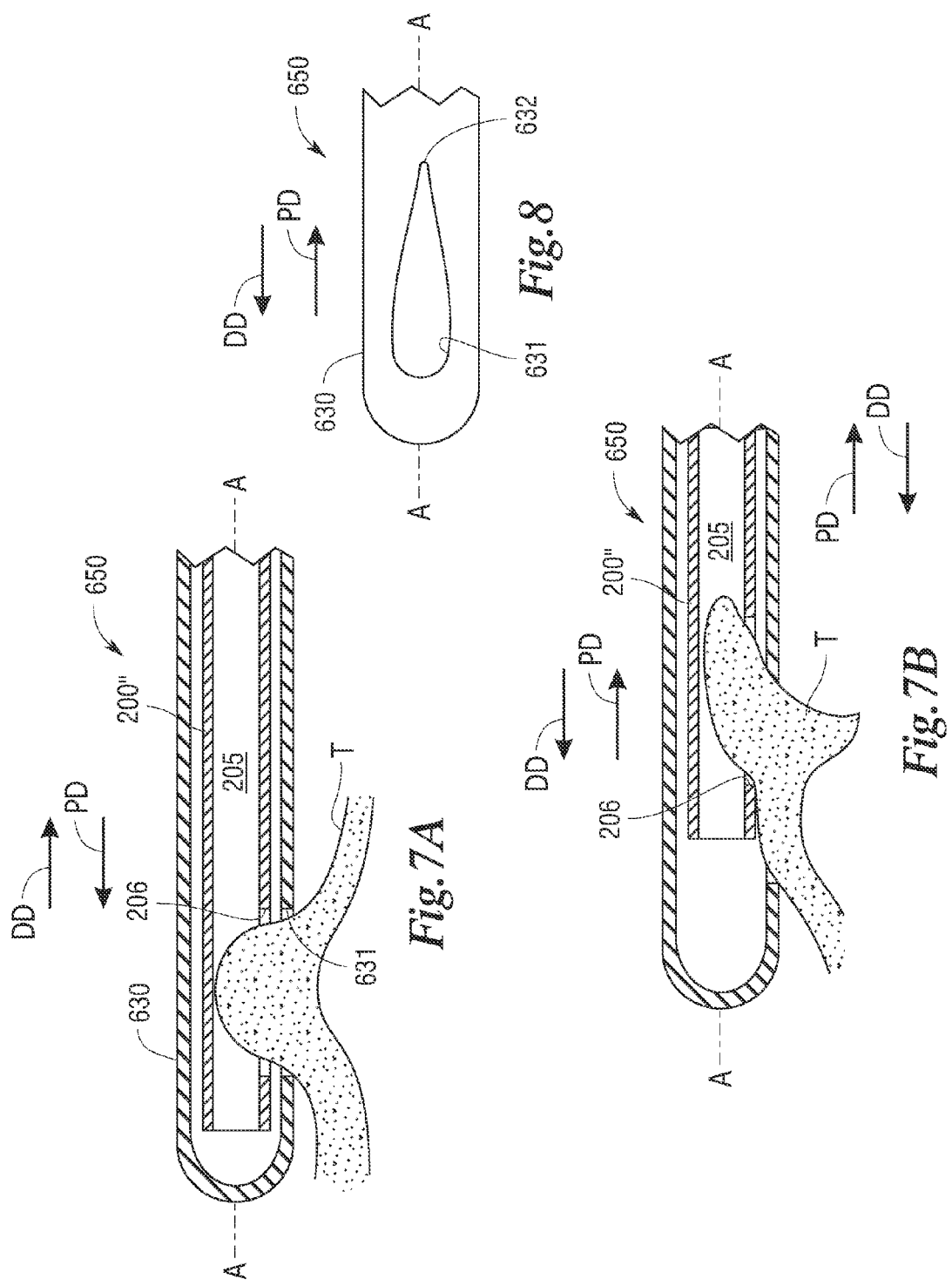

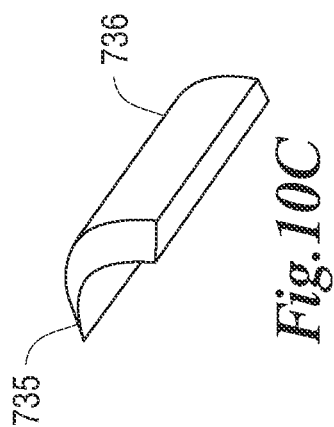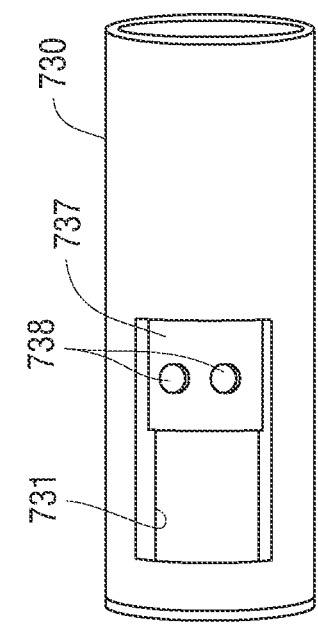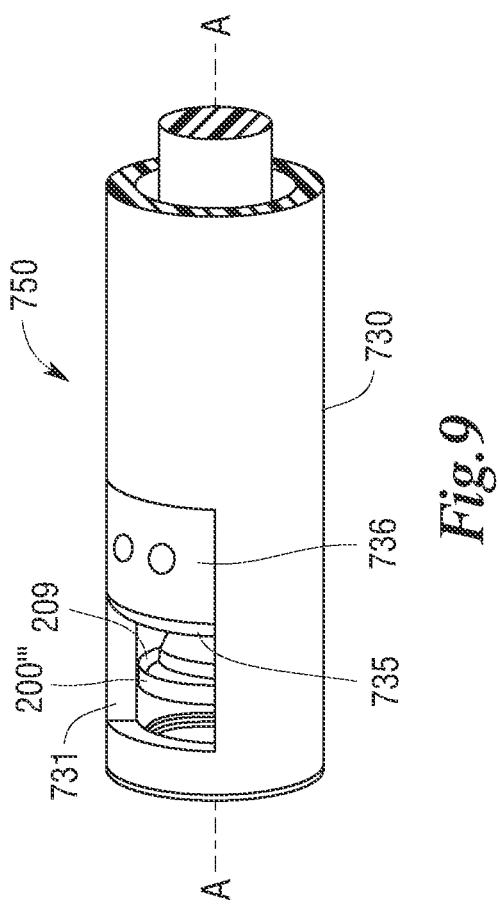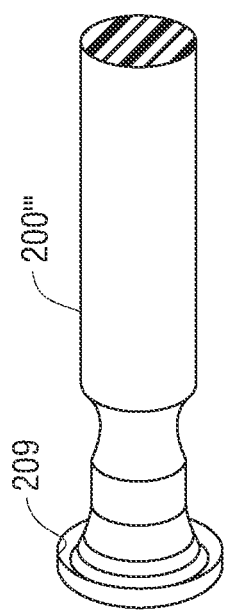

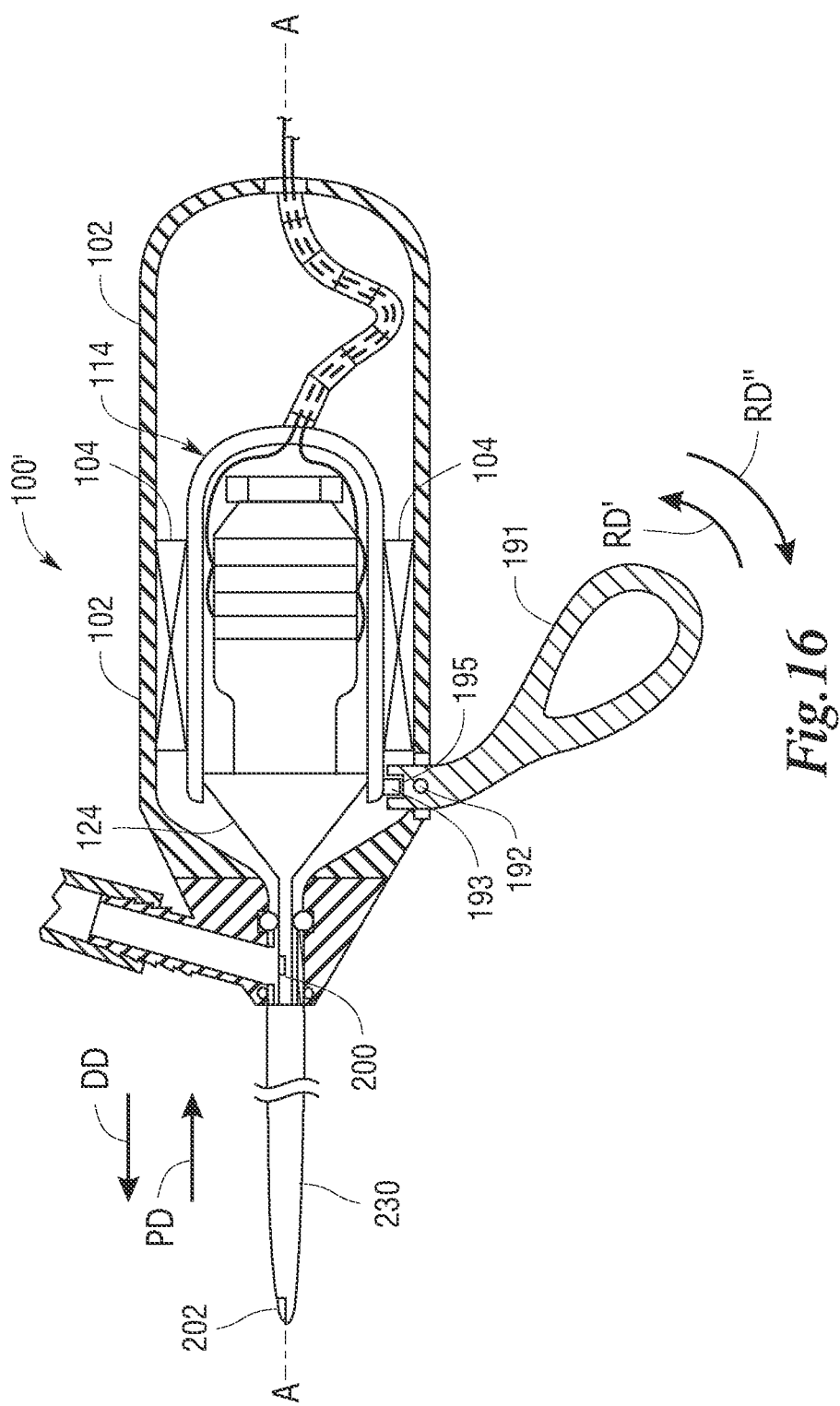

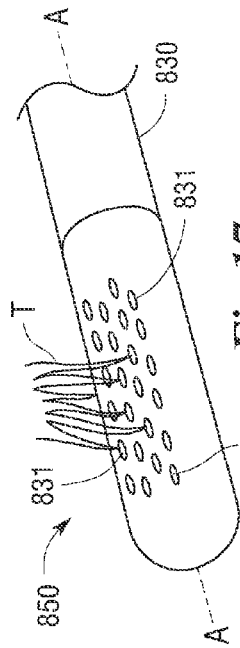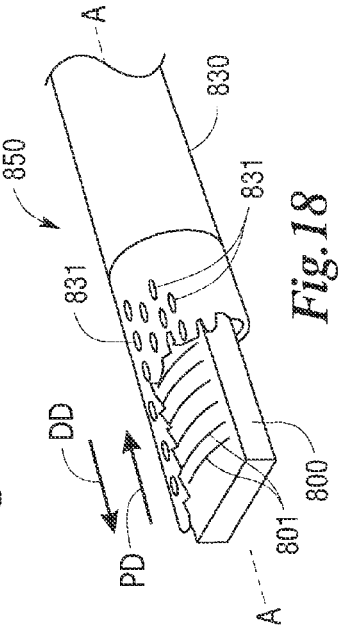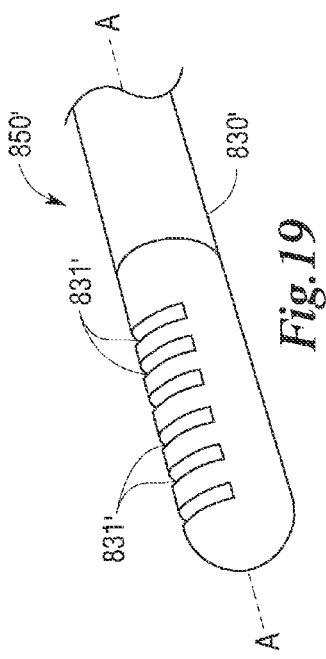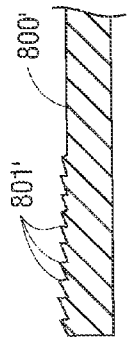

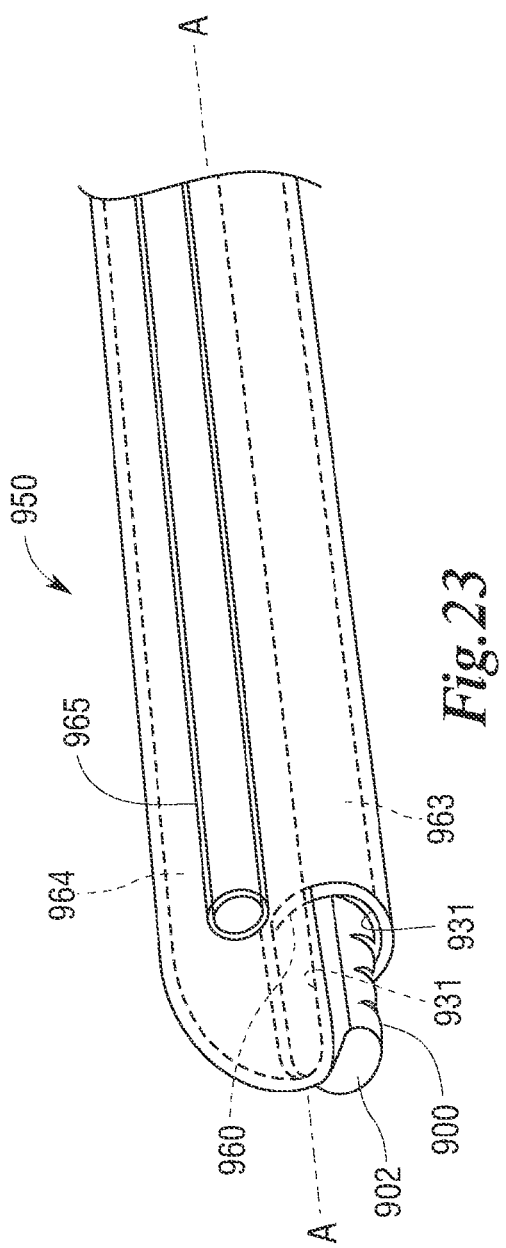
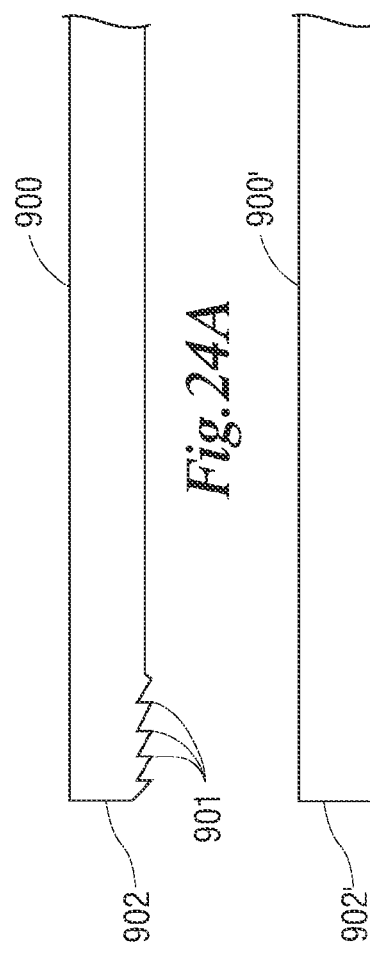
Fig. 23
Fig. 24A
Fig. 24B

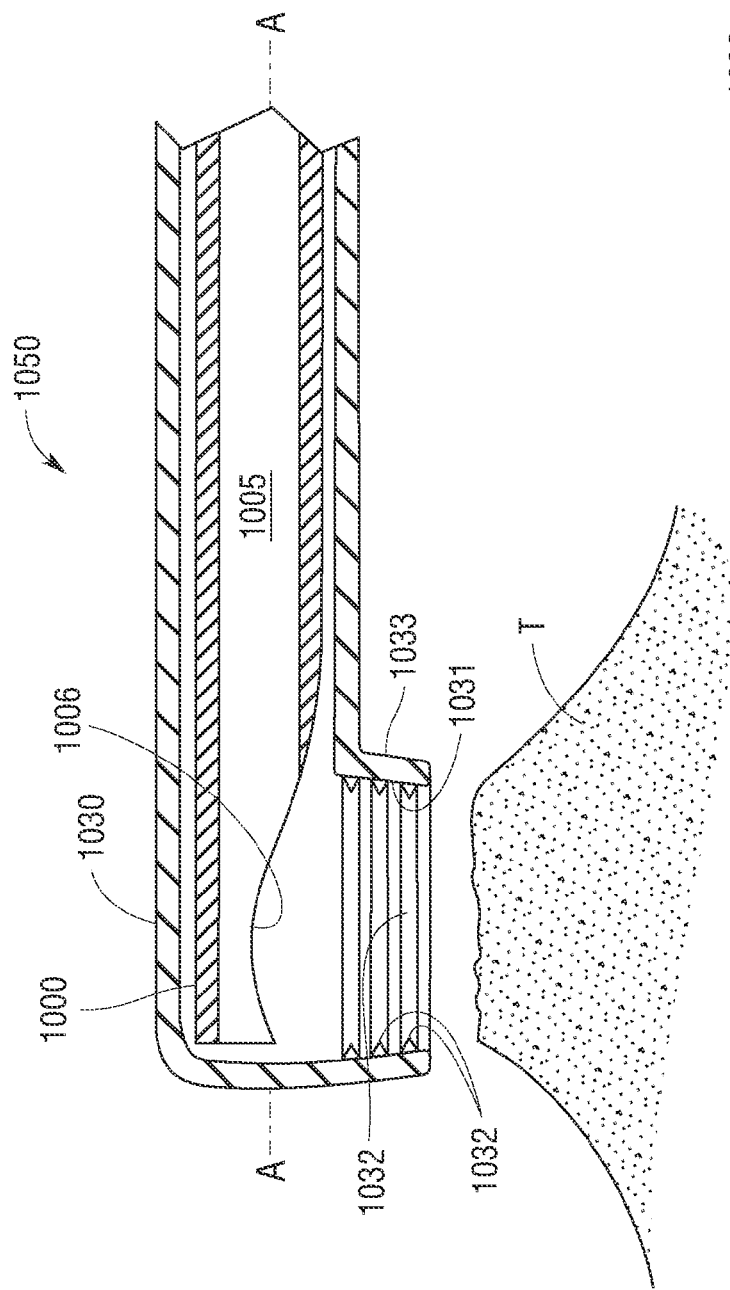
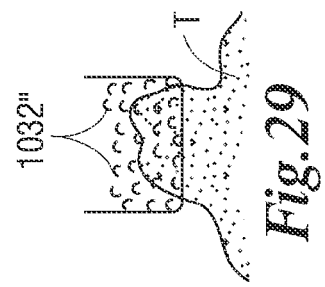
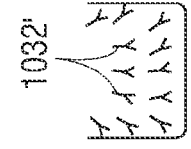
Fig.27
Fig.28
Fig.29

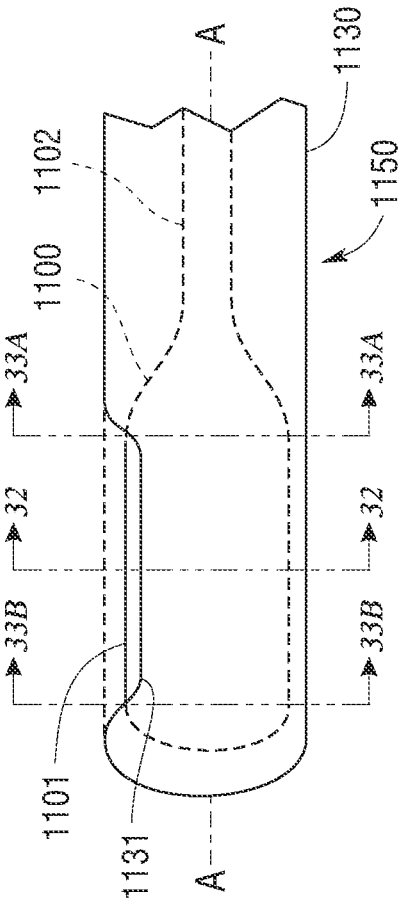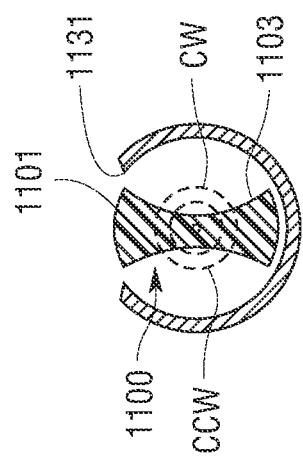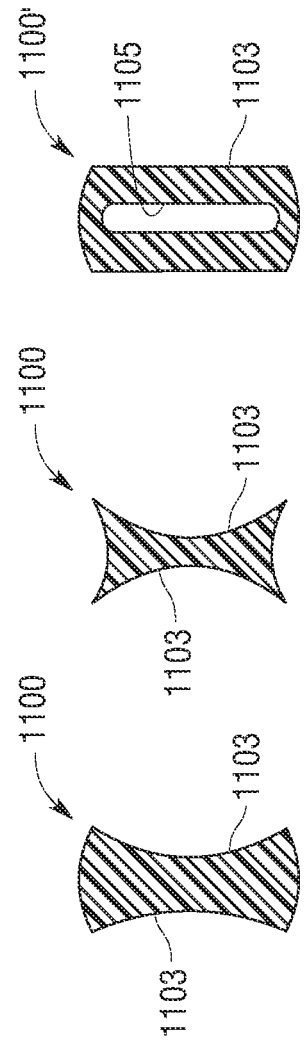

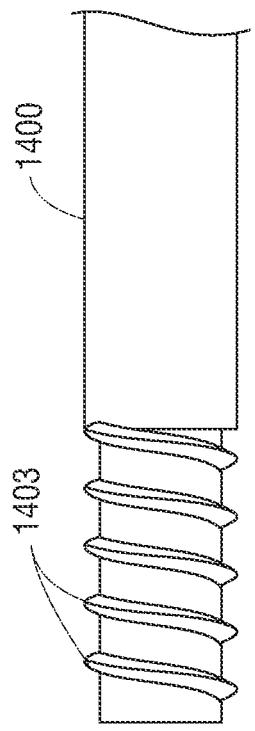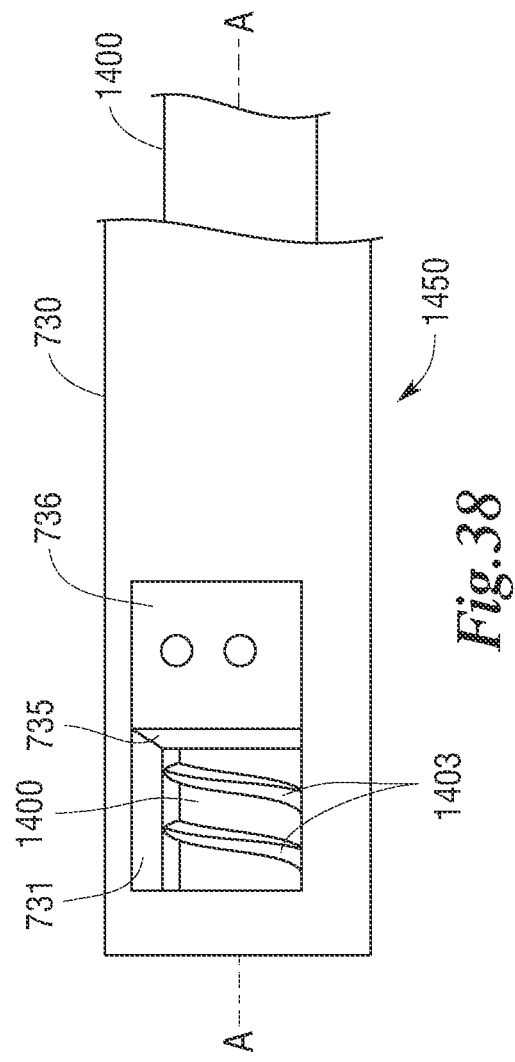

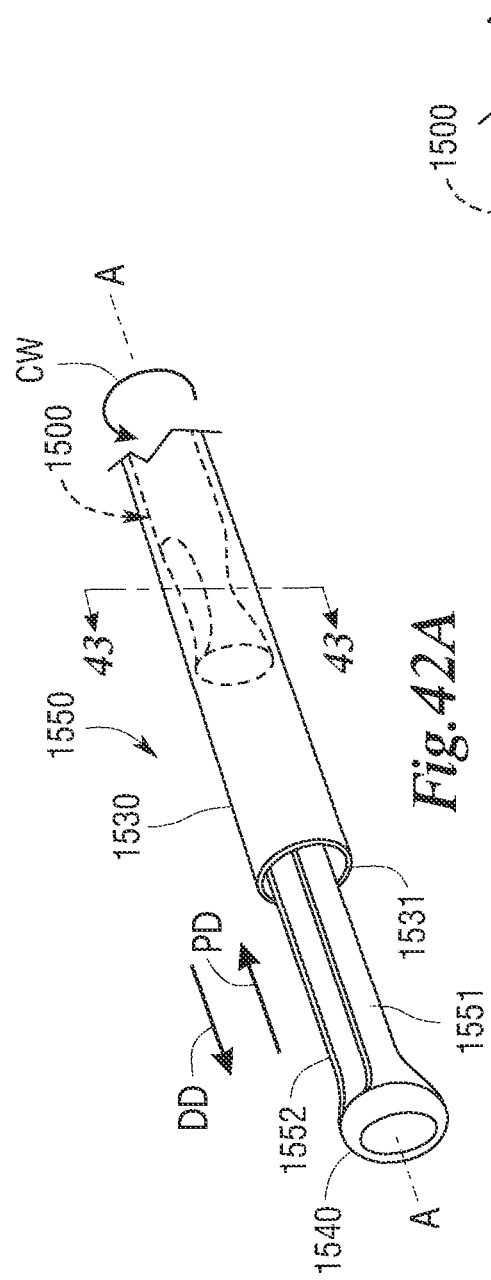
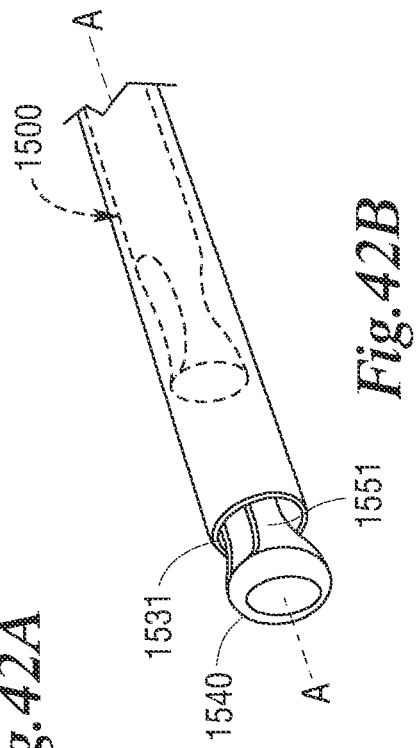
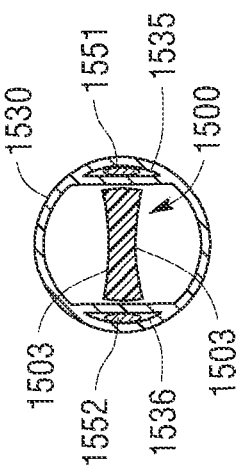
Fig. 42A
Fig. 42B
Fig. 43 ately 25, 30 or 35 kHz. The ultrasonic transducer 14, which is known as a "Langevin stack", generally includes a transduction portion 18, a first resonator 20, and a second resonator 22, forming a resonant acoustic assembly. The ultrasonic transducer 14 is preferably an integral number of one-half system wavelengths (nλ/2) in length as will be described in more detail later. An acoustic assembly 24 includes the ultrasonic transducer 14, nose cone 26, velocity transformer 28, and surface 30.

ULTRASONIC SURGICAL INSTRUMENTS WITH MOVING CUTTING IMPLEMENT

BACKGROUND

The present disclosure generally relates to ultrasonic surgical systems and, more particularly, to ultrasonic systems that allow surgeons to perform cutting and coagulation of tissue.

Over the years, a variety of different types of non-ultrasonically powered cutters and shaving devices for performing surgical procedures have been developed. Some of these devices employ a rotary cutting instrument and other devices employ a reciprocating cutting member. For example, shavers are widely used in arthroscopic surgery. Arthroscopic surgery involves performing surgery in the joint space. To perform the surgery, the joints are commonly filled with pressurized saline for distention and visualization.

The aforementioned devices generally consist of a power supply, a handpiece, and a single-use end effector. The end effector commonly has an inner and outer tube. The inner tube rotates relative to the outer tube and will cut tissue with its sharpened edges. The inner tube can rotate continuously or oscillate. In addition, such device may employ a suction channel that travels through the interior of the inner tube. For example, U.S. Pat. No. 4,850,354 to McGurk-Burleson, et al., discloses a non-ultrasonically powered surgical cutting instrument that comprises a rotary cutter for cutting material with a shearing action. It employs an inner cutting member which is rotatable within an outer tube.

U.S. Pat. No. 3,776,238 to Peyman et al. discloses an ophthalmic instrument in which tissue is cut by a chopping action set-up by the sharp end of an inner tube moving against the inner surface of the end of an outer tube. U.S. Pat. No. 5,226,910 to Kajiyama et al. discloses another surgical cutting instrument that has an inner member which moves relative to an outer member to cut tissue entering through an aperture in the outer member.

U.S. Pat. No. 4,922,902 to Wuchinich et al. discloses a method and apparatus for endoscopic removal of tissue utilizing an ultrasonic aspirator. The device uses an ultrasonic probe which disintegrates compliant tissue and aspirates it through a narrow orifice. U.S. Pat. No. 4,634,420 to Spinosa et al. discloses an apparatus and method for removing tissue from an animal and includes an elongated instrument having a needle or probe, which is vibrated at an ultrasonic frequency in the lateral direction. The ultrasonic movement of the needle breaks-up the tissue into fragments. Pieces of tissue can be removed from the area of treatment by aspiration through a conduit in the needle. U.S. Pat. No. 3,805,787 to Banko discloses yet another ultrasonic instrument that has a probe that is shielded to narrow the beam of ultrasonic energy radiated from the tip of the probe. In one embodiment the shield extends past the free-end of the probe to prevent the probe from coming into contact with the tissue. U.S. Pat. No. 5,213, 569 to Davis discloses a phaco-emulsification needle which focuses the ultrasonic energy. The focusing surfaces can be beveled, curved or faceted. U.S. Pat. No. 6,984,220 to Wuchinich and U.S. Patent Publication No. US 2005/0177184 to Easley disclose ultrasonic tissue dissection systems that provide combined longitudinal and torsional motion through the use of longitudinal-torsional resonators. U.S Patent Publication No. US 2006/0030797 A1 to Zhou et al. discloses an orthopedic surgical device that has a driving motor for driving an ultrasound transducer and horn. An adapter is provided between the driving motor and transducer for supplying ultrasonic energy signals to the transducer.

While the use of ultrasonically powered surgical instruments provide several advantages over traditional mechanically powered saws, drills, and other instruments, temperature rise in bone and adjacent tissue due to frictional heating at the bone/tissue interface can still be a significant problem. Current arthroscopic surgical tools include punches, reciprocating shavers and radio frequency (RF) devices. Mechanical devices such as punches and shavers create minimal tissue damage, but can sometimes leave behind ragged cut lines, which are undesirable. RF devices can create smoother cut lines and also ablate large volumes of soft tissue; however, they tend to create more tissue damage than mechanical means. Thus, devices which could provide increased cutting precision while forming smooth cutting surfaces without creating excessive tissue damage would be desirable.

The foregoing discussion is intended only to illustrate the present field and should not be taken as a disavowal of claim scope.

SUMMARY

In various embodiments, a surgical instrument is provided. In at least one embodiment, the surgical instrument can comprise a hollow sheath, a blade disposed at least partially within the hollow sheath, at least one ultrasonic transducer operably coupled to the blade, and a drive system. In these embodiments, the drive system can communicate with the transducer to deliver axial motions to the blade such that the blade translates with respect to the hollow sheath when the drive system is activated.

In at least one embodiment, a surgical instrument is provided that can comprise a hollow sheath, a blade disposed at least partially within the hollow sheath, at least one ultrasonic transducer coupled to the blade, and a drive system. In these embodiments, the drive system can communicate with the transducer to deliver rotational motions to the blade such that the blade rotates with respect to the hollow sheath when the drive system is activated. Further, in these embodiments, the hollow sheath can include at least one opening therein and at least one tooth positioned in the opening. Moreover, in these embodiments, the tooth can be configured to grip tissue positioned within the opening.

In at least one embodiment, a surgical instrument is provided that can comprise a hollow sheath including at least one opening therein, a blade disposed at least partially within the hollow sheath, an ultrasonic transducer coupled to the blade, a tissue gripping member movably supported by the hollow shaft, and a drive system coupled to the tissue gripping member. In these embodiments, the drive system can be configured to deliver axial motions to the tissue gripping member such that the tissue gripping member translates with respect to the hollow sheath when the drive system is activated.

BRIEF DESCRIPTION OF THE FIGURES

The novel features of the embodiments described herein are set forth with particularity in the appended claims. The embodiments, however, both as to organization and methods of operation may be better understood by reference to the following description, taken in conjunction with the accompanying drawings as follows.

FIG. 7A is a side cross-section view of a distal portion of a non-limiting embodiment of a surgical instrument; a blade of the instrument is shown in a first axial position.

FIG. 7B is another side cross-sectional view of the distal portion of the surgical instrument of FIG. 7A; the blade is shown translated axially to a second axial position.

FIG. 8 is a top view of the distal portion of the surgical instrument of FIG. 7A.

FIG. 9 is a perspective view of a distal portion of a non-limiting embodiment of a surgical instrument.

FIG. 10A is a perspective view of a distal portion of a hollow sheath of the surgical instrument of FIG. 9.

FIG. 10B is a perspective view of a distal portion of a blade of the surgical instrument of FIG. 9.

FIG. 10C is a perspective view of a shearing plate of the surgical instrument of FIG. 9.

FIG. 16 is a partial cross-sectional view of a non-limiting embodiment of a surgical instrument employing another linear drive system.

FIG. 17 is a perspective view of a distal portion of a non-limiting embodiment of a surgical instrument including a plurality of openings in a hollow sheath; tissue is shown being drawn into the openings.

FIG. 18 is a partial cutaway view of the distal portion of the surgical instrument of FIG. 17, showing a toothed blade.

FIG. 19 is a perspective view of a distal portion of another non-limiting embodiment of a surgical instrument including a plurality of openings in a hollow sheath.

FIGS. 20A-20B are side cross-sectional views of distal portions of toothed blades for use in a surgical instrument, such as the surgical instruments of FIGS. 17-19.

FIGS. 21A-21C are side cross-sectional views of individual teeth that may be used with a toothed blade.

FIG. 23 is a perspective view of a distal portion of the surgical instrument of FIG. 22.

FIGS. 24A and 24B are side views of distal portions of blades for a surgical instrument, such as the surgical instrument of FIG. 22.

FIG. 27 is a side cross-sectional view of a distal portion of a non-limiting embodiment of a surgical instrument including teeth defined in an opening of a hollow sheath for gripping tissue.

FIGS. 28-29 are partial views of teeth that may be used in a surgical instrument, such as the surgical instrument of FIG. 27.

FIG. 31 is a side view of a distal portion of a non-limiting embodiment of a surgical instrument including a rotatable blade.

FIG. 32 is a cross-section view of the surgical instrument of FIG. 31, taken along line 32-32.

FIG. 33A is a cross-section view of the blade of the surgical instrument of FIG. 31, taken along line 33A-33A.

FIG. 33B is a cross-sectional view of the blade of the surgical instrument of FIG. 31, taken along line 33B-33B.

FIG. 34 is a cross-section view of another non-limiting embodiment of a blade for a surgical instrument, such as the surgical instrument of FIG. 31.

FIG. 38 is a top view of a distal portion of a non-limiting embodiment of a surgical instrument including a blade with a screw surface.

FIG. 39 is a top view of the distal portion of the blade of the surgical instrument of FIG. 38.

FIG. 42A is a perspective view of a distal portion of the surgical instrument of FIG. 40; the tissue gripping member is shown in an extended position.

FIG. 42B is a perspective view of the distal portion of the surgical instrument of FIG. 40; the tissue gripping member is shown in a retracted position.

FIG. 43 is a cross-section view of the hollow sheath, cables, and blade of the surgical instrument of FIG. 40, taken along line 43-43 in FIG. 42A.

DETAILED DESCRIPTION

Figure 1:
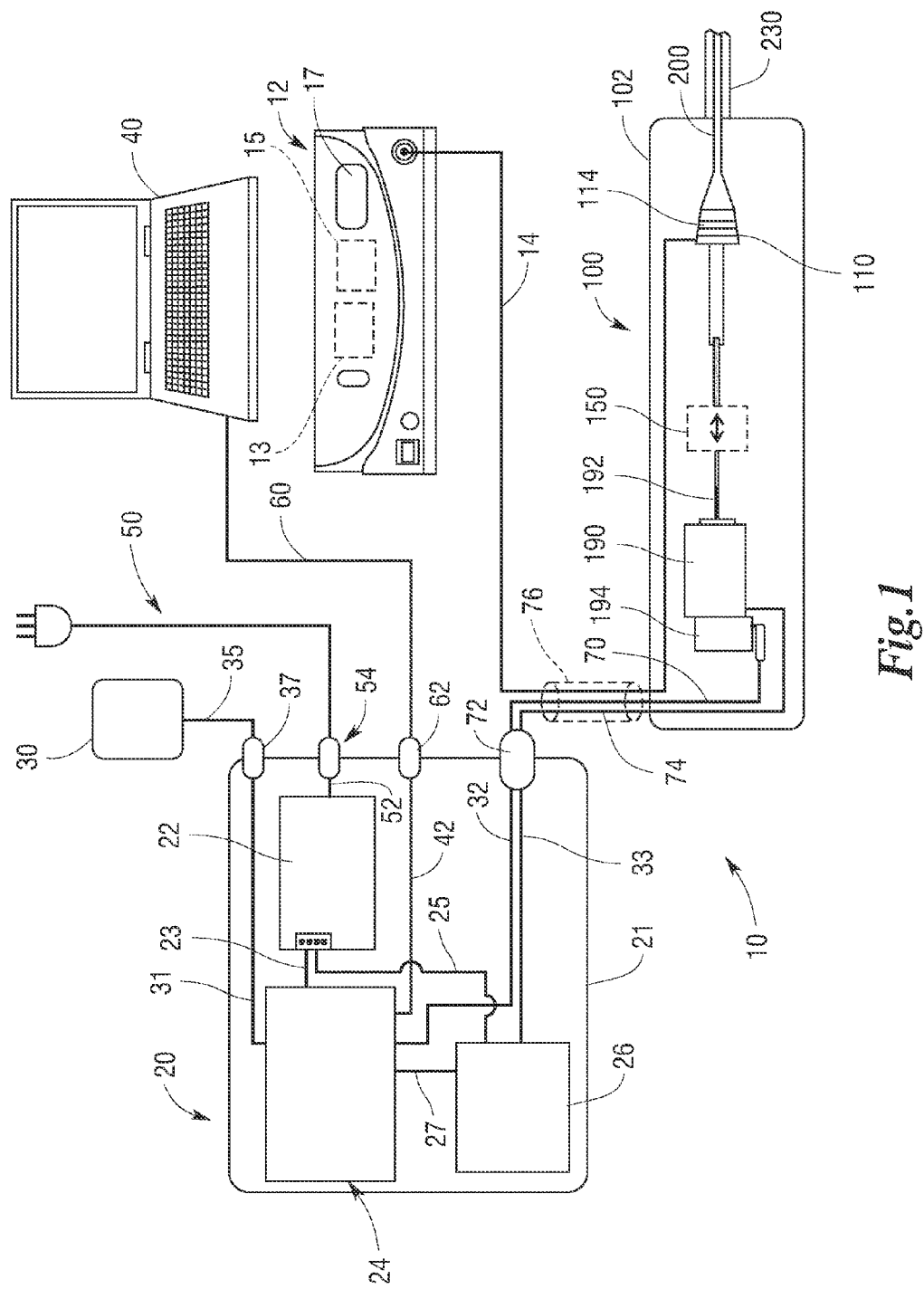
FIG. 1 is a schematic view of a non-limiting embodiment of a surgical control system embodiment.

The owner of the present application also owns the following U.S. patent applications that were filed on even date herewith and which are herein incorporated by reference in their respective entireties:

U.S. patent application Ser. No. 12/703,860, entitled ULTRASONICALLY POWERED SURGICAL INSTRUMENTS WITH ROTATING CUTTING IMPLEMENT;

U.S. patent application Ser. No. 12/703,864, entitled METHODS OF USING ULTRASONICALLY POWERED SURGICAL INSTRUMENTS WITH ROTATABLE CUTTING IMPLEMENTS;

U.S. patent application Ser. No. 12/703,866, entitled SEAL ARRANGEMENTS FOR ULTRASONICALLY POWERED SURGICAL INSTRUMENTS;

U.S. patent application Ser. No. 12/703,870, entitled ULTRASONIC SURGICAL INSTRUMENTS WITH ROTATABLE BLADE AND HOLLOW SHEATH ARRANGEMENTS;

U.S. patent application Serial No. 12/703,875, entitled ROTATABLE CUTTING IMPLEMENT ARRANGEMENTS FOR ULTRASONIC SURGICAL INSTRUMENTS;

U.S. patent application Ser. No. 12/703,877, entitled ULTRASONIC SURGICAL INSTRUMENTS WITH PARTIALLY ROTATING BLADE AND FIXED PAD ARRANGEMENT;

U.S. patent application Ser. No. 12/703,879, entitled DUAL PURPOSE SURGICAL INSTRUMENT FOR CUTTING AND COAGULATING TISSUE;

U.S. patent application Ser. No. 12/703,885, entitled OUTER SHEATH AND BLADE ARRANGEMENTS FOR ULTRASONIC SURGICAL INSTRUMENTS; and U.S. patent application Ser. No. 12/703,899, entitled ULTRASONIC SURGICAL INSTRUMENT WITH COMB-LIKE TISSUE TRIMMING DEVICE.

Certain embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting embodiments and that the scope of these embodiments is defined solely by the claims. The features illustrated or described in connection with one embodiment may be combined with the features of other embodiments. Further, where an ordering of steps in a process is indicated, such ordering may be rearranged or the steps may be carried out contemporaneously as desired unless illogical or the listed order is explicitly required. Such modifications and variations are intended to be included within the scope of the appended claims.

In the following description, like reference characters designate like or corresponding parts throughout the several views. Also in the following description, it is to be understood that terms such as "forward," "rearward," "front," "back," "right," "left," "over," "under," "top," "bottom," "upwardly," "downwardly," "proximally," "distally," and the like are words of convenience and are not to be construed as limiting terms. The description below is for the purpose of describing various embodiments and is not intended to limit the appended claims.

Various embodiments are directed to improved ultrasonic surgical systems and instruments configured for effecting tissue dissecting, cutting, and/or coagulation during surgical procedures as well as the cutting implements employed thereby. In one embodiment, an ultrasonic surgical instrument apparatus is configured for use in open surgical procedures, but has applications in other types of surgery, such as laparoscopic, endoscopic, and robotic-assisted procedures. Versatile use is facilitated by selective use of ultrasonic energy, the selective gross axial and/or rotational motion of the cutting/coagulation implement, and/or suction applied near and/or through the cutting/coagulation implement.

It will be appreciated that the terms "proximal" and "distal" are used herein with reference to a clinician gripping a handpiece assembly. Thus, an end effector is distal with respect to the more proximal handpiece assembly. It will be further appreciated that, for convenience and clarity, spatial terms such as "top" and "bottom" also are used herein with respect to the clinician gripping the handpiece assembly. However, surgical instruments are used in many orientations and positions, and these terms are not intended to be limiting and absolute.

FIG. 1 illustrates in schematic form one non-limiting embodiment of a surgical system 10. The surgical system 10 may include an ultrasonic generator 12 and an ultrasonic surgical instrument assembly 100 that may include ultrasonic producing components. As will be discussed in further detail below, the ultrasonic generator 12 may be connected by a cable 14 to an ultrasonic transducer assembly 114 in a housing portion 102 of the surgical instrument assembly 100. The transducer assembly 114 may include one or more ultrasonic transducers capable of producing ultrasonic vibrations. Further, attached to the ultrasonic transducer assembly 114 may be a horn 124 for amplifying and/or focusing ultrasonic motions created by the transducer assembly 114. Coupled to the horn 124 may be a blade 200 disposed at least partially within a hollow sheath 230 extending from the housing portion 102. In one embodiment, the system 10 further includes a motor control system 20 that includes a power supply 22 that is coupled to a control module 24 by cable 23 to supply, for example, 24 VDC thereto. The motor control module 24 may comprise a control module manufactured by National Instruments under Model No. NI cRIO-9073. However, other motor control modules may be employed. Any of a number of power supplies may be successfully employed for power supply 22. The power supply 22 may be further coupled to a motor drive 26 by cable 25 to also supply 24 VDC thereto. The motor drive 26 may comprise a motor drive manufactured by National Instruments. However, other motor drives may be successfully employed. Control module 24 may also be coupled to the motor drive 26 by cable 27 for supplying power thereto. A conventional foot pedal 30 or other control switch arrangement may be attached to the control module 24 by a cable 31. As will be discussed in further detail below, the ultrasonic surgical instrument 100 may include a drive system that may include a motor 190 that has an encoder 194 associated therewith. The drive system may communicate with the transducer assembly 114, via a rotational-to-linear motion converter 150 (described below), to deliver gross axial motions to the blade 200 such that the blade translates with respect to the hollow sheath when the drive system is activated. The motor 190 may comprise a motor manufactured by National Instruments under Model No. CTP12ELF10MAA00. However, other motors may be employed. The encoder 194 may comprise a linear encoder manufactured by US Digital under Model No. E2-500-197-I-D-D-B. However, other motors and encoders may be used. The encoder 194 may be coupled to the motor control module 24 by an encoder cable 32 and the motor 190 may be coupled to the motor drive 26 by cable 33. The surgical system 10 may also include a computer 40 that may communicate by Ethernet cable 42 with the motor control module 24.

As can also be seen in FIG. 1, in various embodiments, the motor control system 20 may be housed in an enclosure 21. To facilitate easy portability of the system, various components may be attached to the motor control system 20 by removable cable connectors. For example, foot pedal switch 30 may be attached to a detachable cable connector 37 by cable 35 to facilitate quick attachment of the foot pedal to the control system 20. A/C power may be supplied to the power supply 22 by a conventional plug/cable 50 that is attached to a detachable cable connector 54 that is attached to cable 52. The computer 40 may have a cable 60 that is attached to detachable cable connector 62 that is coupled to cable 42. The encoder 194 may have an encoder cable 70 that is attached to a detachable connector 72. Likewise, the motor 190 may have a cable 74 that is attached to the detachable connector 72. The detachable connector 72 may be attached to the control module 24 by cable 32 and the connector 72 may be attached to the motor drive 26 by cable 33. Thus, cable connector 72 serves to couple the encoder 194 to the control module 24 and the motor 190 to the motor drive 26. The cables 70 and 74 may be housed in a common sheath 76.

Figure 1A:
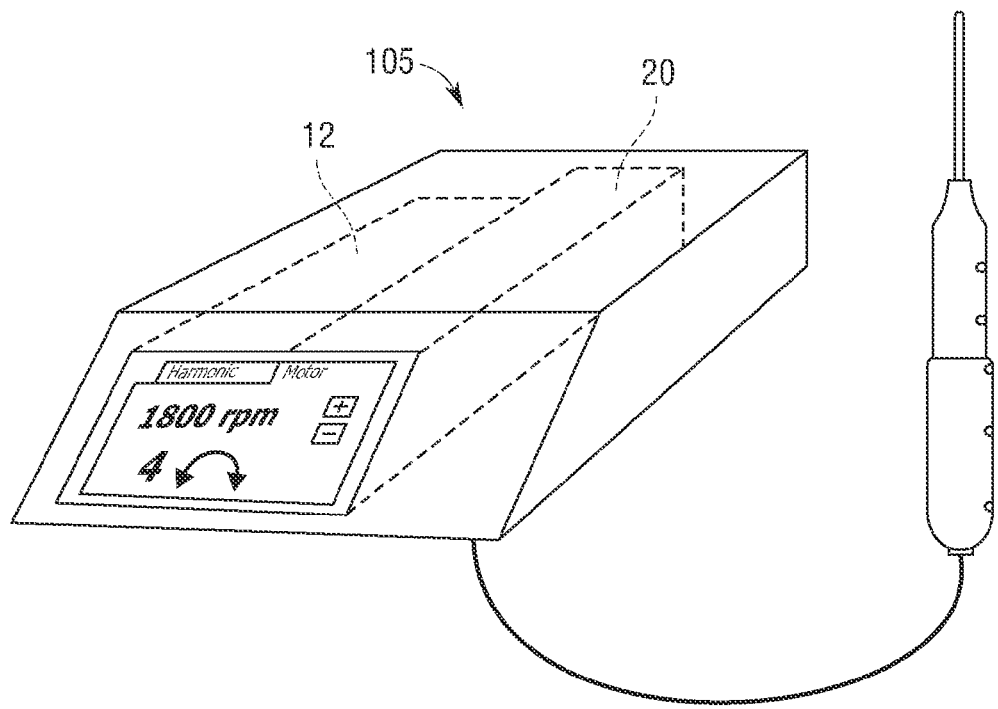
FIG. 1A is a perspective view of a non-limiting embodiment of a control system enclosure.
Figure 1B:
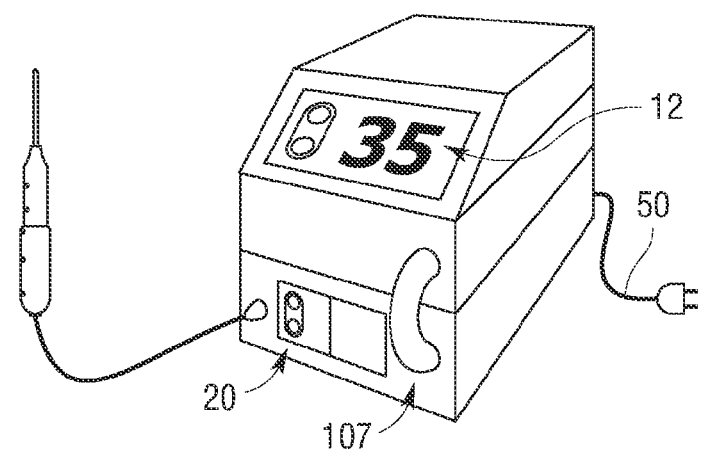
FIG. 1B is a perspective view of another non-limiting embodiment of a control system enclosure arrangement.

In an alternative embodiment, the ultrasonic generator 12 and the control system 20 may be housed in the same enclosure 105. See FIG. 1A. In yet another embodiment, the ultrasonic generator 12 may electrically communicate with the motor control system 20 by a jumper cable 107. Such arrangement may share a data link as well as a common means for supplying power (cord 50). See FIG. 1B.

In various embodiments, the ultrasonic generator 12 may include an ultrasonic generator module 13 and a signal generator module 15. See FIG. 1. The ultrasonic generator module 13 and/or the signal generator module 15 each may be integrated with the ultrasonic generator 12 or may be provided as separate circuit modules electrically coupled to the ultrasonic generator 12 (shown in phantom to illustrate this option). In one embodiment, the signal generator module 15 may be formed integrally with the ultrasonic generator module 13. The ultrasonic generator 12 may comprise an input device 17 located on a front panel of the generator 12 console. The input device 17 may comprise any suitable device that generates signals suitable for programming the operation of the generator 12 in a known manner. Still with reference to FIG. 1, the cable 14 may comprise multiple electrical conductors, such as copper wires, for the application of electrical energy to positive (+) and negative (−) electrodes of an ultrasonic transducer assembly 114 as will be discussed in further detail below.

Various forms of ultrasonic generators, ultrasonic generator modules and signal generator modules are known. For example, such devices are disclosed in commonly owned U.S. patent application Ser. No. 12/503,770, entitled Rotating Transducer Mount For Ultrasonic Surgical Instruments, filed Jul. 15, 2007, which is herein incorporated by reference in its entirety. Other such devices are disclosed in one or more of the following U.S. patents, all of which are incorporated by reference herein: U.S. Pat. No. 6,480,796 (Method for Improving the Start Up of an Ultrasonic System Under Zero Load Conditions); U.S. Pat. No. 6,537,291 (Method for Detecting a Loose Blade in a Handle Connected to an Ultrasonic Surgical System); U.S. Pat. No. 6,626,926 (Method for Driving an Ultrasonic System to Improve Acquisition of Blade Resonance Frequency at Startup); U.S. Pat. No. 6,633,234 (Method for Detecting Blade Breakage Using Rate and/or Impedance Information); U.S. Pat. No. 6,662,127 (Method for Detecting Presence of a Blade in an Ultrasonic System); U.S. Pat. No. 6,678,621 (Output Displacement Control Using Phase Margin in an Ultrasonic Surgical Handle); U.S. Pat. No. 6,679,899 (Method for Detecting Transverse Vibrations in an Ultrasonic Handle); U.S. Pat. No. 6,908,472 (Apparatus and Method for Altering Generator Functions in an Ultrasonic Surgical System); U.S. Pat. No. 6,977,495 (Detection Circuitry for Surgical Handpiece System); U.S. Pat. No. 7,077,853 (Method for Calculating Transducer Capacitance to Determine Transducer Temperature); U.S. Pat. No. 7,179,271 (Method for Driving an Ultrasonic System to Improve Acquisition of Blade Resonance Frequency at Startup); and U.S. Pat. No. 7,273,483 (Apparatus and Method for Alerting Generator Function in an Ultrasonic Surgical System).

Figure 2:
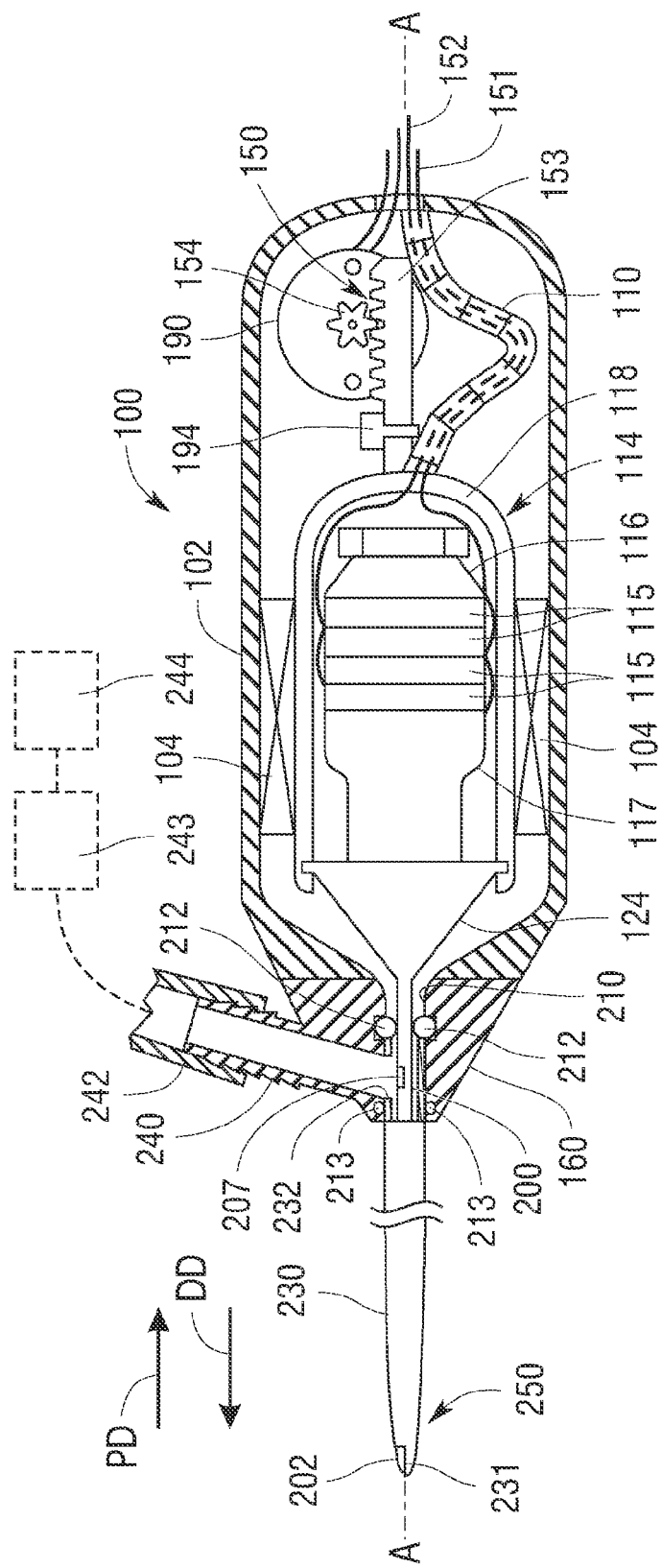
FIG. 2 is a partial cross-sectional view of a non-limiting embodiment of a handheld surgical instrument employing a linear drive system.

As can be seen in FIG. 2, an ultrasonic surgical instrument 100 may comprise a housing 102 that houses the motor 190, the encoder 194, the ultrasonic transducer assembly 114, and the horn 124. The transducer assembly 114 may be movably supported within the housing 102 by conventional linear bearings 104, such as rollers. Extending from the horn 124 may be the blade 200, which passes through the hollow sheath 230 to a window or opening 231 defined therein. As shown in FIG. 2, a distal end 202 of the blade 200 may be seen through the opening 231 at a distal portion 250 of the surgical instrument 100. The housing 102 may be provided in two or more parts that are attached together by fasteners such as screws, snap features, etc. and/or by one or more adhesives and may be fabricated from, for example, polycarbonate, stainless steel, or other material. The motor 190 may be mounted to the housing 102 and may mechanically communicate with the ultrasonic transducer by way of a rotational-to-linear motion converter 150, which may comprise a rack member 153 and a pinion 154. Additional gears may be added between the pinion 154 and the rack member 153 to achieve desired gear reductions, if desired. Further, the rack member 153 may hold the encoder 194 and be attached to the transducer assembly 114. Accordingly, activation of the motor 190 may turn pinion 154, and thus drive rack 153, encoder 194, transducer assembly 114, horn 124, and blade 200 in a proximal direction "PD" or a distal direction "DD" parallel to or coaxial with the hollow sheath's longitudinal axis A-A. The motor 190 may comprise, for example, a stepper motor manufactured by National Instruments under Model No. CTP12ELF10MAA00. However, other motors, such as brushless DC or other types, may be employed to effectuate, for example, "gross" axial motion of the blade 200 relative to the hollow sheath 230 on the order of 1 to 15 mm. The encoder 194 may convert the position and/or speed of the rack member 154 into electrical pulses that provide position, speed, and/or other control information to the control module 24. Further, the encoder 194 may include an in-line force sensor (not shown), such as a piezoelectric sensor, that may measure a load experienced by the blade's distal end 202 and communicated to the rack member 153, such as the load provided by tissue when the surgical instrument is used in a surgical operation.

Referring still to FIG. 2, the ultrasonic transducer assembly 114 may include a housing 118 that supports piezoelectric ultrasonic transducers 115 for converting electrical energy to mechanical energy that results in longitudinal vibrational motion of the ends of the transducers 115. The ultrasonic transducers 115 may comprise a stack of ceramic piezoelectric elements with a motion null point located at some point along the stack. The ultrasonic transducers 115 may be mounted between a proximal end piece 116 and a distal end piece 117. In addition, the horn 124 may be mounted to the distal end piece 117 at the null point on one side and to the blade 200 on the other side. As a result, the blade 200 will vibrate in the longitudinal direction at an ultrasonic frequency rate with the ultrasonic transducer assembly 114. The ends of the ultrasonic transducer assembly 114 achieve maximum motion with a portion of the stack constituting a motionless node, when the ultrasonic transducer assembly 114 is driven at maximum current at the transducer's resonant frequency.

However, the current providing the maximum motion will vary with each instrument and is a value stored in the non-volatile memory of the instrument so the system can use it.

The parts of the surgical instrument 100 may be designed such that the combination will oscillate at the same resonant frequency. In particular, the elements may be tuned such that the resulting length of each such element is one-half wavelength or a multiple thereof. Longitudinal back and forth motion is amplified as the diameter closer to the blade 200 of the acoustical mounting horn 124 decreases. Thus, the horn 124 as well as the blade 200 may be shaped and dimensioned so as to amplify blade motion and provide ultrasonic vibration in resonance with the rest of the acoustic system, which produces the maximum back and forth motion of the end of the acoustical mounting horn 124 close to the blade 200. A motion from 20 to 25 microns at the ultrasonic transducers 115 may be amplified by the horn 124 into blade movement of about 40 to 100 microns.

Referring briefly back to FIG. 1, when power is applied to the ultrasonic instrument 110 by operation of the foot pedal 30 or other switch arrangement, the control system 20 may, for example, cause the blade 200 to vibrate longitudinally at approximately 55.5 kHz, and the amount of longitudinal movement will vary proportionately with the amount of driving power (current) applied, as adjustably selected by the user. When relatively high cutting power is applied, the blade 200 may be designed to move longitudinally in the range of about 40 to 100 microns at the ultrasonic vibrational rate. Such ultrasonic vibration of the blade 200 will generate heat as the blade contacts tissue, i.e., the acceleration of the blade 200 through the tissue converts the mechanical energy of the moving blade 200 to thermal energy in a very narrow and localized area. This localized heat creates a narrow zone of coagulation, which will reduce or eliminate bleeding in small vessels, such as those less than one millimeter in diameter. The cutting efficiency of the blade 200, as well as the degree of hemostasis, will vary with the level of driving power applied, the cutting rate or force applied by the surgeon to the blade, the nature of the tissue type, and the vascularity of the tissue.

Referring again to FIG. 2, when power is applied to motor 190, motor 190, via pinion 154, applies a "gross axial motion" to the rack member 153 to cause the ultrasonic transducer assembly 114 and blade 200 to translate with respect to the hollow sheath 230. As used herein, the term "gross axial motion," and the like, is to be distinguished from "ultrasonic motion," and the like, that may be achieved by way of the ultrasonic transducer assembly. The term "gross axial motion" instead encompasses translational motion that is not solely generated by operation of the ultrasonic transducer assembly 114.

To provide the ultrasonic instrument 110 with power from the ultrasonic generator 12 (see FIG. 1), a multiple-segment jointed protector 110 may be employed. As can be seen in FIG. 2, conductors 151, 152 are coupled to the ultrasonic transducer assembly 114 and extend out of the instrument through the housing 102. Further, the protector 110 may be attached to the instrument housing 102 at one end and to the transducer assembly housing 118 at the other end. The conductors 151, 152 may pass through one or more holes in the transducer assembly housing. Accordingly, ultrasonic signals from the ultrasonic generator 12 are transferred to the ultrasonic transducers 115 through the conductors 151, 152. The protector 110 may prevent the conductors 151, 152 from being damaged or pinched by the mechanical components of the instrument 100 when the motor 190 is activated.

Referring still to FIG. 2, various embodiments also include a distal nosepiece 160 that may be removably attached to the distal end of the housing 102 by fasteners and/or adhesives (not shown). The nosepiece 160 may be fabricated from, for example, stainless steel, aluminum, or plastic. In various embodiments, the distal end 202 of the blade 200 extends through a hollow portion 210 of the nosepiece 160. The hollow sheath 230 may likewise extend through the hollow portion 210. The hollow portion 210 may include an annular groove in which a proximal seal 212 may be held against the end of the hollow sheath 230 and against the blade 200. The seal 212 may comprise, for example, a silicone O-ring, a brazing, or a press-fit seal, and serve to establish a substantially fluid-tight and/or airtight seal between the nosepiece 160, blade 200, and hollow sheath 230.

Also in various embodiments, the hollow sheath 230 may be coaxially aligned with the blade 200 and be attached to the hollow portion 210 of the nosepiece 160 by, for example, welding, press-fitting, threading, adhering with glue or other adhesive(s), etc. As can be seen in FIG. 2, a suction port 240 may be attached to the nosepiece 160 to communicate with a proximal hole 232 in the hollow sheath 230. A flexible tube 242 may be attached to the suction port 240 and communicate with a collection receptacle 243 that is coupled to a source of vacuum, generally depicted as 244. Thus, the hollow sheath 230 forms a suction path extending around the blade 200 that begins at the distal portion 250 of the outer sheath 230, such as at the opening 231, and goes out through the hole 232 to the suction port 240. Those of ordinary skill in the art will appreciate that alternate suction paths are also possible. Further, a distal seal 213, similar to proximal seal 212, may be held in the nosepiece 160 and may help further seal the hollow sheath 230 therein such that the suction path from the opening 231, through the sheath 230, out hole 232, and through the port 240 is maintained with minimal or no ingress of air from outside the aforementioned path.

Various embodiments of the surgical system 10 (see FIG. 1) provide the ability to selectively apply ultrasonic axial motion to the blade 200 and gross axial motion to the blade 200 as well. If desired, the clinician may simply activate the ultrasonic transducer assembly 114 without activating the motor 190. In such cases, the instrument 100 may be used in ultrasonic mode simply as an ultrasonic instrument. Frequency ranges for longitudinal ultrasonic motion may be on the order of, for example, 30-80 kHz. Similarly, the clinician may desire to activate the motor 190 without activating the ultrasonic transducer assembly 114. Thus, gross axial motion will be applied to the blade 200 in the translational mode, without the application of longitudinal ultrasonic motion thereto. Gross axial speeds may be, for example, on the order of 0.25 in/s to 5 in/s. In other applications, the clinician may desire to use the instrument 100 in the ultrasonic and translational modes wherein the blade 200 will experience longitudinal ultrasonic motion from the transducer assembly 114 and gross axial motion from the motor 190. Further, the blade 200 may translate back and forth within the hollow sheath 230 by reversing the output of the motor. By way of example, the motor 190 may first cause the blade 200 to move in the distal direction DD. The encoder 194 may then sense or calculate when the blade 200 has reached the distal end of the hollow sheath 230 and then provide feedback causing the motor 190 to reverse, thereby moving the blade 200 in the proximal direction PD until the encoder 194 again senses or calculates that the blade 200 has moved sufficiently in the proximal direction PD, and then the encoder 194 may again provide feedback causing the motor to reverse again. Various such gross translational oscillatory or reciprocating motions may thereby be achieved. Moreover, those of ordinary skill in the art will readily appreciate that various embodiments of the surgical system 10 may be affectively employed in connection with arthroscopic as well as other surgical applications.

Figure 3:
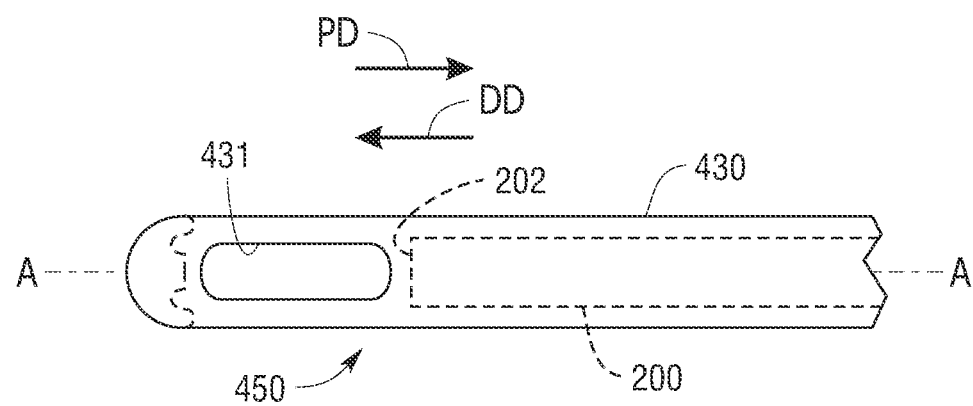
FIG. 3 is a top view of a distal portion of a non-limiting embodiment of a surgical instrument.
Figure 4:
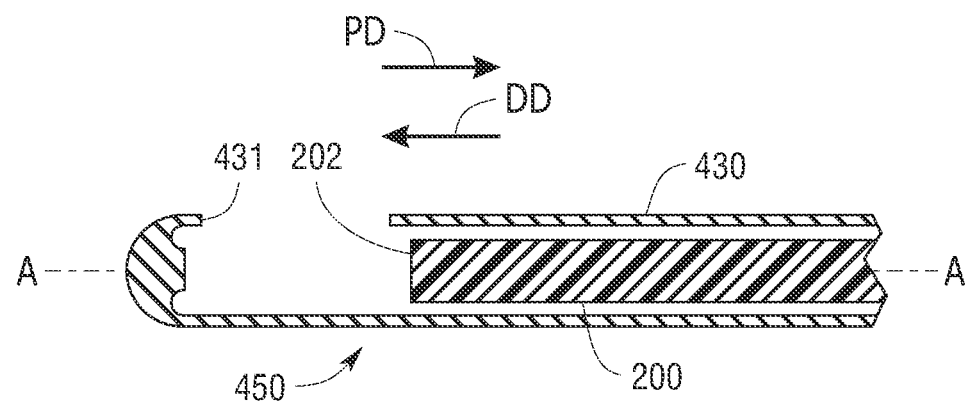
FIG. 4 is a side cross-sectional view of the distal portion of the surgical instrument of FIG. 3.

The surgical instrument 100 may have various distal portions 250. FIGS. 3 and 4 illustrate an example of a distal portion 450 of another non-limiting embodiment of a surgical instrument wherein like numbers previously used to describe the various embodiments disclosed above are used to designate like components. In these embodiments, the surgical instrument includes a hollow sheath 430, a blade 200 disposed at least partially within the hollow sheath 430, an ultrasonic transducer (not shown, see transducers 115 in FIG. 2) operably coupled to the blade, and a drive system (also not shown, see motor 190 in FIG. 2) communicating with the transducer to deliver axial motions to the blade 200 such that the blade 200 translates, for example in the proximal and distal directions, PD and DD, respectively, with respect to the hollow sheath 430 when the drive system is activated. In such embodiments, the blade 200 may have a tube-like shape and may cut tissue when the same is drawn into and/or through the opening 431 of the hollow sheath 430 by suction therethrough. Accordingly, tissue that is drawn into the sheath 430 may be cut by activating the ultrasonic transducers to create ultrasonic motion of the blade 200 and/or by activating the motor to cause the blade 200 to translate with gross axial motion with respect to the hollow sheath 430. The distal end 202 of the blade 200 may be shaped to enhance cutting by having a sharp edge or a scalloped shape. The latter shape may assist in the cutting of tough tissues.

Figure 5:
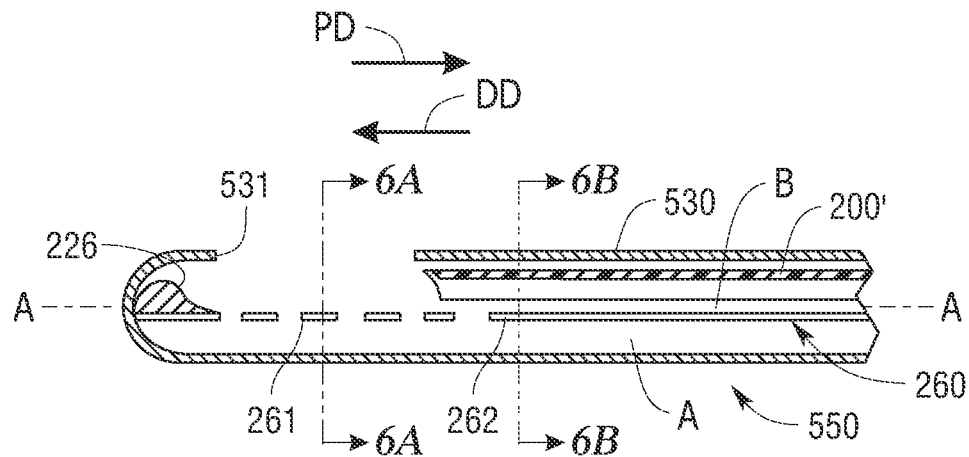
FIG. 5 is a side cross-section view of a distal portion of a non-limiting embodiment of a surgical instrument.
Figure 6A:
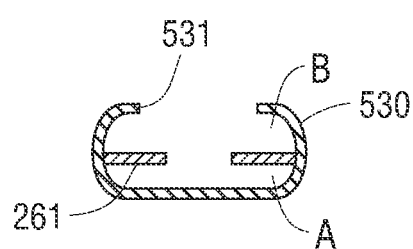
FIG. 6A is a front cross-sectional view of the distal portion of the surgical instrument of FIG. 5, taken along line 6A-6A.
Figure 6B:
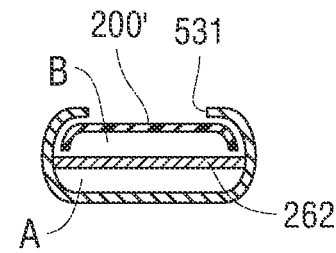
FIG. 6B is another front cross-sectional view of the distal portion of the surgical instrument of FIG. 5, taken along line 6B-6B.
Figure 11:
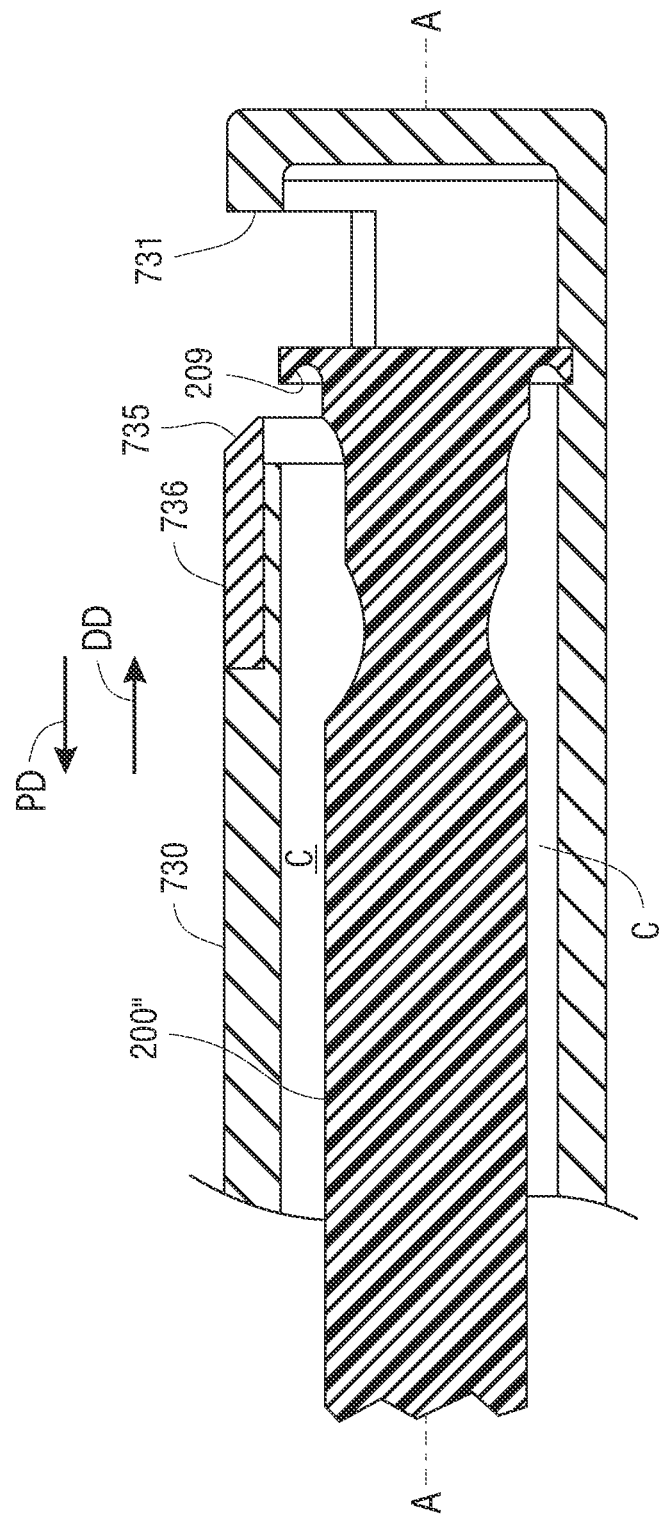
FIG. 11 is a side cross-sectional view of the distal portion of the surgical instrument of FIG. 9.

FIGS. 5-6B illustrate another example of a distal portion 550 of another non-limiting embodiment of a surgical instrument wherein like numbers previously used to describe the various embodiments disclosed above are used to designate like components. FIG. 5 is a cross-sectional view taken along a longitudinal axis of the hollow sheath 530 and FIGS. 6A and 6B are cross-sectional views taken along their respective lines in FIG. 5. In these embodiments, a septum 260 may divide the interior of the hollow sheath 530 into a suction portion "A" and a blade portion "B." The suction portion A may communicate with a suction port (not shown, see port 240, described above). Further, the septum 260 may be divided into a perforated portion 261 and a solid portion 262, both of which may be integrally formed with the hollow sheath 530. Alternatively, all of the septum 260 may be perforated. In any event, suction may be applied to the instrument such that, during a surgical operation, tissue is pulled toward suction portion A, by way of the perforated portion 261. Such configurations may help properly position tissue through opening 531 such that the blade 200' may be moved into and cut the tissue held therethrough. Further, referring to FIG. 5, a pad 226 may be fixed to the sheath 530 and/or to the septum 260 to provide a cutting surface against which the blade 200' may cut tissue, when the blade 200' is moved into contact therewith. Also, as can be seen in FIG. 6B, the blade 200' may include a U-shape to reduce mass.

Referring still to FIGS. 5-6B, in at least one embodiment, tissue may be cut as follows. First, suction may be applied to the suction portion A of the hollow sheath 530 such that tissue is drawn into the opening 531. Second, the ultrasonic transducers may cause the blade 200' to vibrate ultrasonically. Third, the blade 200' may be advanced in the distal direction DD such that the blade 200' cuts the tissue by both gross axially movement and ultrasonic vibrational movement. Third, the blade 200' may be retracted while suction is maintained, thereby capturing and/or drawing the severed tissue into the suction portion A of the hollow sheath 530.

FIGS. 7A-8 illustrate another example of a distal portion 650 of another non-limiting embodiment of a surgical instrument wherein like numbers previously used to describe the various embodiments disclosed above are used to designate like components. FIGS. 7A and 7B are longitudinal cross-sectional views of the instrument's distal portion 650, with the blade 200" in a first position in FIG. 7A and in a second position in FIG. 7B. FIG. 8 is a top view of the distal portion 650 showing a teardrop-shaped opening 631 in hollow sheath 630. In these embodiments, the blade 200" may further include a lumen 205 through which suction may also be applied. Accordingly, the blade 200" may include a distal aperture 206 and a proximal aperture 207 (see FIG. 2). As best seen in FIG. 2, the proximal aperture 207 may be positioned within the nosepiece 160 (see FIG. 2). In any event, referring back to FIGS. 7A-7B, suction may be applied through the lumen 205 such that tissue "T" may be drawn into the blade 200" via distal aperture 206 when the blade 200" is in the first axial position, see FIG. 7A. After the tissue is drawn into the blade 200" (see FIG. 7A), the tissue T may be pinched between the distal aperture 206 and a narrow portion 632 of the opening 631 by translating the blade 200" in the proximal direction to the second axial position, see FIG. 7B. Thereafter, the tissue may be cut by activating the ultrasonic transducer(s), as described above. The opening's narrow portion 632, combined with the pinching of the tissue therein, may help more easily sever tissue with the ultrasonic vibrational motion of the blade 200".

FIGS. 9-12C illustrate another example of a distal portion 750 of another non-limiting embodiment of a surgical instrument wherein like numbers previously used to describe the various embodiments disclosed above are used to designate like components. In these embodiments, the hollow sheath 730 may further include a beveled shearing surface 735 against which the blade 200''' may cut tissue at opening 731. The beveled shearing surface 735 may be similar to a single tooth in that it provides a sharpened edge against which tissue may be cut. FIG. 9 is a perspective view of the distal portion 750 of the surgical instrument. FIG. 10A is a perspective view of the distal portion of the hollow sheath, FIG. 10B is a perspective view of the distal portion of the blade 200''', and FIG. 10C is a perspective view of a shearing plate 736. The shearing surface 735 may be integrally formed with or attached to the sheath 730. In at least one embodiment, the shearing surface 735 may be formed from a portion of a shearing plate 736. In such embodiments, the shearing plate may be held in place on the hollow sheath 200''' via press pins, epoxy, snap features, etc. As seen in FIG. 10A, the hollow sheath 730 may include a recess 737 and protrusions 738 extending therefrom for receiving the plate 736. Further, as best seen in the cross-sectional view provided in FIG. 11, the blade 200''' may further include a sharpened surface 209 that is complimentary to the beveled shearing surface 735. Also, proximal to the sharpened surface 209, sufficient clearance "C" may exist between the blade 200''' and the inner surface of the hollow sheath 730 such that suction may communicate from the suction port (not shown, see port 240 in FIG. 2) to the opening 731. Further, the clearance C may be large enough to allow tissue to be drawn through the hollow sheath 730 between the blade 200''' and the sheath 730.

Figure 12A:
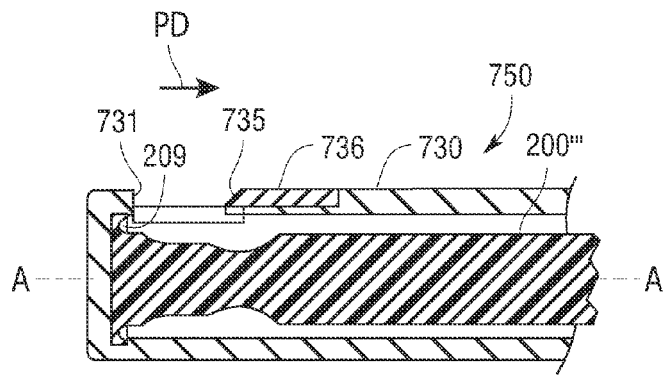
FIGS. 12A-12C are a series of side cross-sectional views of the distal portion of the surgical instrument of FIG. 9 showing the blade in different axial positions as the blade translates with respect to the hollow sheath.
Figure 12B:
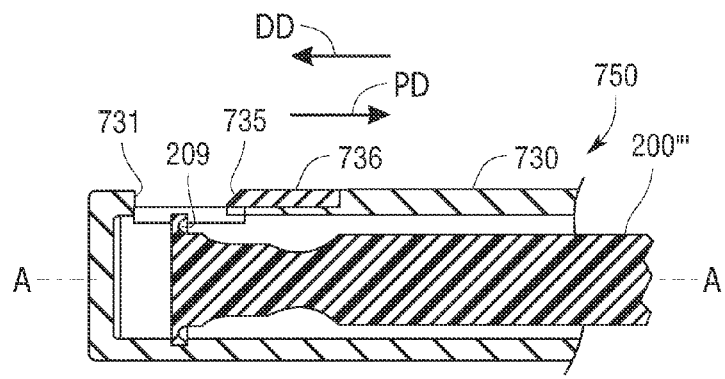
Figure 12C:
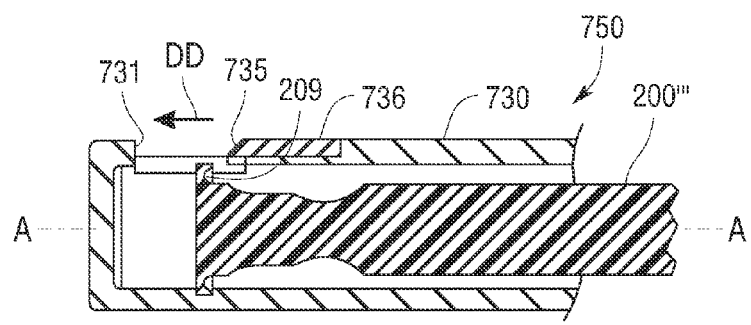

Further, as noted above, the blade 200''' may move axially past the opening 731. For example, FIGS. 12A-12C illustrate a series of side cross-sectional views of the distal portion 750 of the surgical instrument with the blade 200''' in different axial positions as the blade 200''' translates with respect to the hollow sheath 730. FIG. 12A shows the blade 200''' in a distal-most axial position, FIG. 12B shows the blade 200''' in an interim position, and FIG. 12C shows the blade 200''' in a proximal position. In at least one embodiment, the instrument may function as follows. First, as the blade moves axially past the opening 731, the blade 200''' may receive ultrasonic motions from one or more ultrasonic transducers (see transducers 115 in FIG. 2), as described above. Further, before or as the blade is moving, suction may be applied to the hollow sheath 730. As the two shearing surfaces 735, 209 approach one another, they may cut tissue fibrils hanging in the opening 731. The severed tissue fragments may then be moved through the clearance space C between the blade 200''' and the hollow sheath 730 and ultimately evacuated out of the instrument via the suction port, described above.

Figure 13:
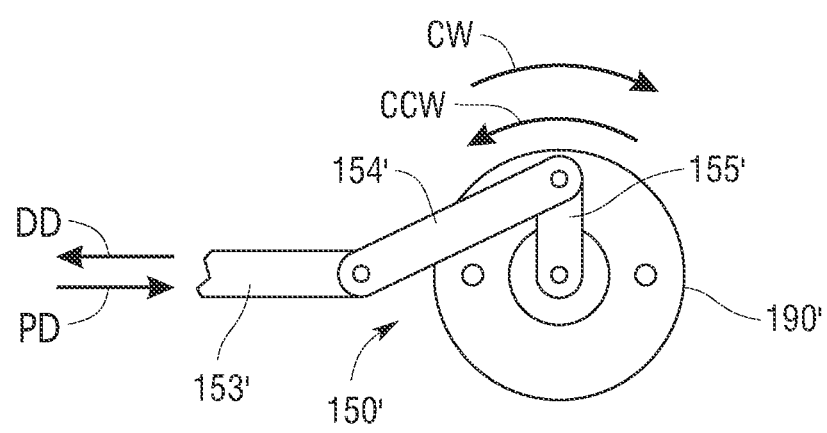
FIG. 13 is a side view of a non-limiting embodiment of a linear drive system for use in a surgical instrument, such as the surgical instrument of FIG. 2.

Referring briefly back to FIG. 2, while the drive system described above utilizes a rack-and-pinion arrangement as the instrument's rotational-to-linear motion converter 150, other converters may be employed. For example, referring now to FIG. 13, a converter 150' may include a slider-crank mechanism configured to transform the rotary drive from the electric motor 190' into linear motion. In such embodiments, the converter 150' may include a slide member 153' coupled to a first crank member 154' which, in turn, is coupled to a second crank member 155' that is attached to the motor's axle. As the motor causes the second crank member 155' to rotate in a clockwise "CW" or counter-clockwise "CCW" direction, the first crank member 154' causes the slide member 153' to slide in the proximal or distal direction, PD or DD, respectively. The slide member 153', which may be coupled to the ultrasonic transducer assembly (see assembly 114 in FIG. 2), may thereby effectuate the gross axial movement of the transducer assembly and thus the blade, as described above. Note that in this and other examples of rotational-to-linear converters described below, various components of the surgical instrument, such as the housing, are omitted for clarity. Additionally, the blade may grossly reciprocate with respect to the hollow sheath because the slide member 153' may move proximally and then distally as the motor 190' rotates the second crank member 155'.

Figure 14:
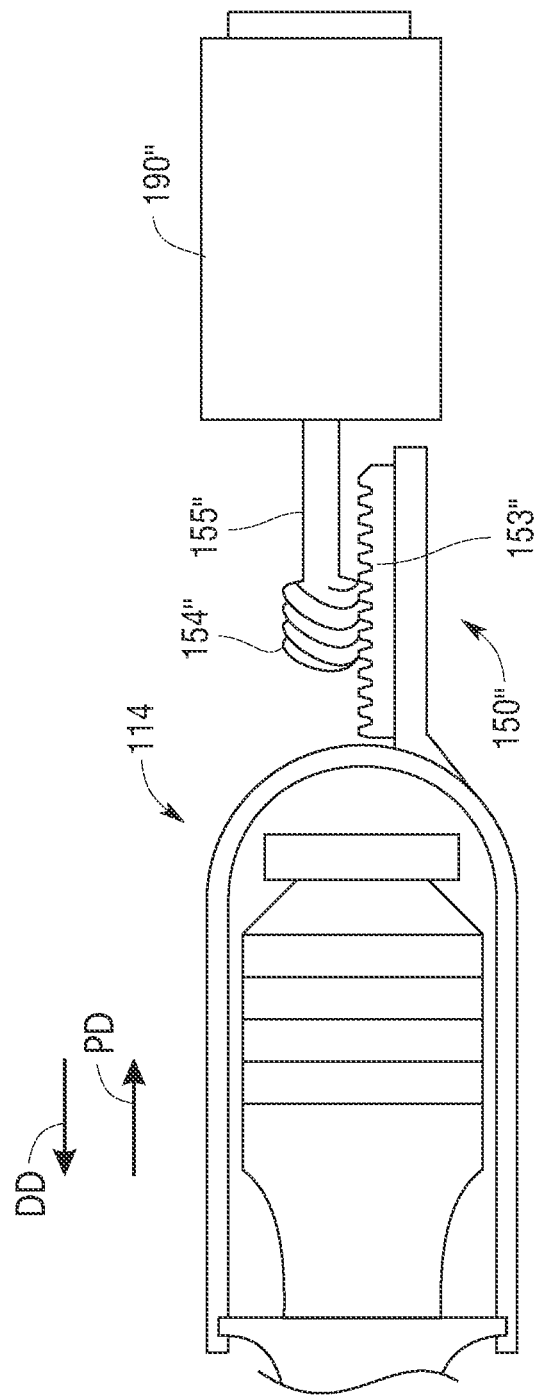
FIG. 14 is a side view of a non-limiting embodiment of another linear drive system for use in a surgical instrument, such as the surgical instrument of FIG. 2.

By way of another example, a rotational-to-linear motion converter 150'' may include a worm gear. Referring to FIG. 14, a motor 190'' is shown with its axle 155'' projecting toward transducer assembly 114. Coupled to the axle 155'' may be a worm gear 154'' that is threadingly engaged with a threaded member 153''. The threaded member 153'' is subsequently coupled to the transducer assembly 114. Accordingly, activation of the motor 190'' may cause the worm gear 154'' to rotate about its axis, thereby driving the threaded assembly 153'', and, thus, ultimately, the transducer assembly 114 and the blade (not shown), in a proximal or distal direction, PD or DD, respectively.

Figure 15:
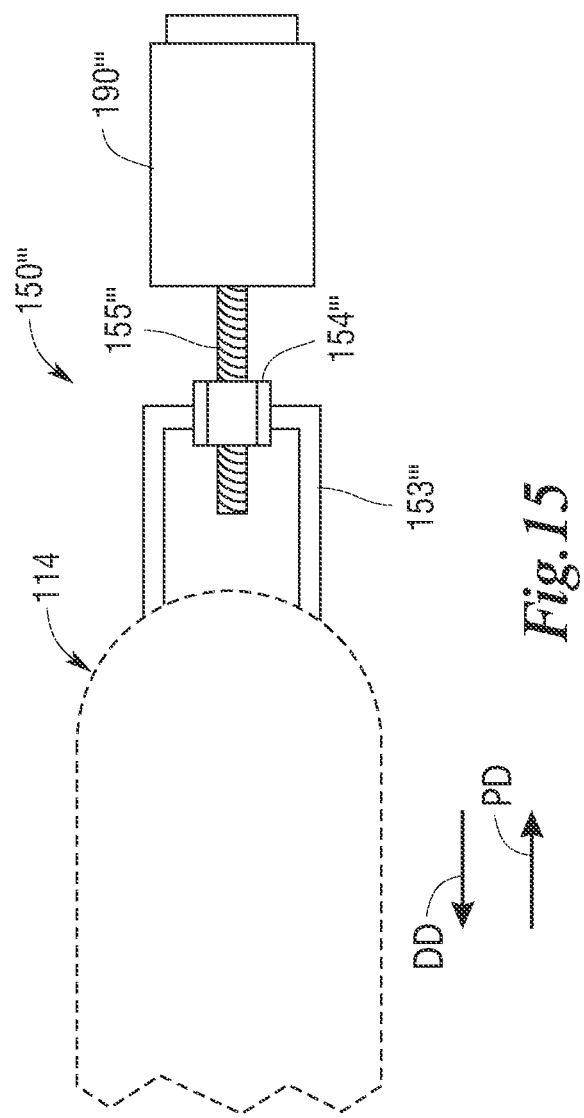
FIG. 15 is a side view of a non-limiting embodiment of another linear drive system for use in a surgical instrument, such as the surgical instrument of FIG. 2.

Another exemplary rotational-to-linear motion converter 150''' may include a lead screw. Referring to FIG. 15, a motor 190''' is shown with a lead screw 155''' serving as its axle. The lead screw 155''' may be threadingly engaged with a nut 154''' that is attached to support members 153'''. Accordingly, activation of the motor 190''' may cause the lead screw 155''' to rotate 154'' about its axis, thereby driving the nut 154''', support members 153''', transducer assembly 114 (shown in phantom), and, ultimately, the blade, in a proximal or distal direction, PD or DD, respectively.

Further, while the above drive systems have utilized a motor, manual drive systems may be used. For example, referring to FIG. 16, another example of a non-limiting embodiment of a surgical instrument 100' is shown wherein like numbers previously used to describe the various embodiments disclosed above are used to designate like components. In these embodiments, a trigger 191 may be pivotally coupled to the housing 102 by a pivot pin 192. The handle may further include a groove 195 in which a projection 193 of the transducer assembly 114 is received. Accordingly, moving the trigger 191 in a first rotational direction RD' may cause the transducer assembly 114 and the blade 200 to move in a distal direction DD. Moving the trigger in a second rotational direction RD'' may also cause the transducer assembly 114 and the blade 200 to move in a proximal direction PD. In use, a user may grasp the housing 102 and activate the trigger 191 with his or her thumb or finger(s).

In various embodiments, other opening configurations at a distal portion of the instrument, such as distal portion 250, see FIG. 2, may be employed. Focusing now on one non-limiting embodiment, FIGS. 17-18 illustrate another example of a distal portion 850 of another non-limiting embodiment of a surgical instrument wherein like numbers previously used to describe the various embodiments disclosed above are used to designate like components. FIG. 17 is a perspective view of the distal portion 850 including a plurality of openings 831 in the hollow sheath 830. Tissue "T" is shown being drawn or drawn into the openings 831 by way of a suction port (not shown, see port 240 in FIG. 2) communicating with the hollow sheath 830. FIG. 18 is a partial cutaway view of the distal portion 850 of the surgical instrument. In these embodiments, the multiple openings 831 may be advantageous over one single opening for pulling the fibrous tissue T therethrough and into contact with blade 800 while stabilizing the tissue T for the blade 800 to cut. The openings 831 may be formed as perforations, or a grid of holes, in the hollow sheath 830. Alternatively, referring to FIG. 19, the openings 831' may be formed as slits in the sheath 830' of the distal portion 850'.

Additionally, in at least one embodiment, the blade 800 may only receive ultrasonic axial movement thereto, as discussed above. Accordingly, a drive system, also as discussed above (including, for instance a motor and/or trigger), may be unnecessary. However, in an alternative embodiment, the blade 800 may receive gross axial motions thereto and be operably coupled to a drive system for moving the blade in proximal or distal directions, PD or DD, respectively, see FIG. 18.

Further, a rasped or toothed blade may further enhance the cutting ability of the instrument. For example, referring to FIG. 18, the blade 800 may include teeth 801 projecting toward and positioned with respect to the openings 831 such that the teeth may contact tissue drawn into the openings 831. The teeth may further have varying profiles. Referring now to FIGS. 20A-21C, a variety of blade teeth profiles, 801', 801'', 801''', 801'''', 801''''', are illustrated. The aforementioned teeth profiles may provide advantageous cutting ability to the blade, such as blades 800, 800', and/or 800''.

Figure 22:
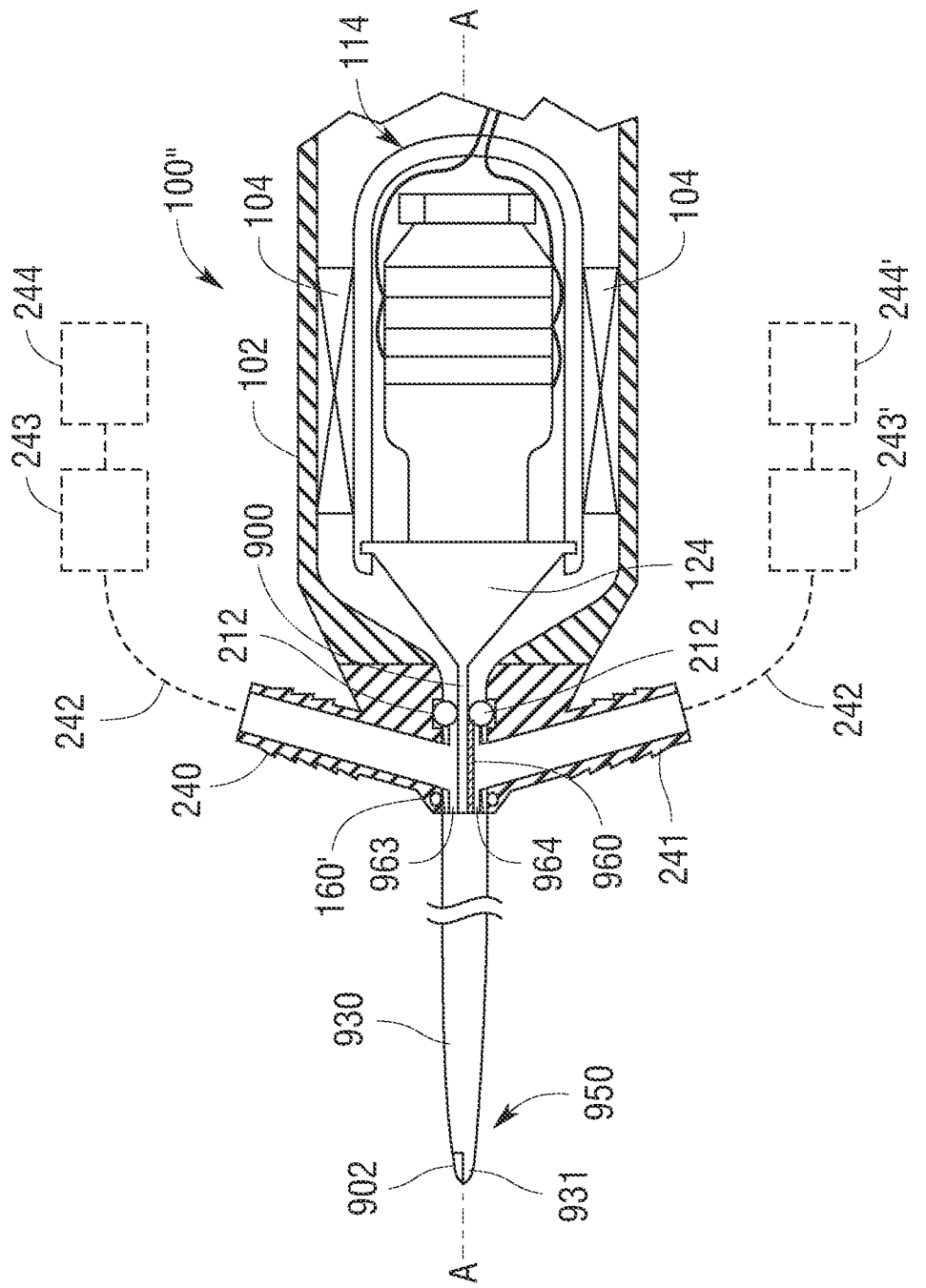
FIG. 22 is a partial cross-sectional view of a non-limiting embodiment of a surgical instrument employing two suction lumens.

While some embodiments described above include one suction port, in various embodiments, other suction configurations may be employed. Focusing now on one non-limiting embodiment, FIGS. 22-23 illustrate another example of a surgical instrument 100'' wherein like numbers previously used to describe the various embodiments disclosed above are used to designate like components. FIG. 22 is a partial cross-sectional view of part of the surgical instrument 100'' employing two suction lumens and two suction ports and FIG. 23 is a perspective view of the distal portion 950 of the surgical instrument 100''. Referring to FIG. 22, the surgical instrument may include a housing 102 containing the transducer assembly 114 coupled to the horn 124, among other things. As discussed above, the horn may subsequently be attached to the blade 900. Additionally, the nose piece 160' may include a first suction port 240 and a second suction port 241 which may be coupled to independent collection receptacles 243, 243' and/or vacuum sources 244, 244' by flexible tubing 242, 242'. The hollow sheath 930 may further include a septum 960 dividing the interior of the hollow sheath into a first lumen 963 and a second lumen 964. The septum 960 may extend to the proximal end of the hollow sheath and abut against proximal seal 212. The first suction port 240 may communicate with the first lumen 963 and the second port 241 may communicate with the second lumen 964. Referring to FIG. 23, the first and second lumens 963 and 964, respectively, can be seen extending to the hollow sheath's opening 931. Accordingly, applying suction to ports 240 and 241 (see FIG. 22) may create two suction paths, via the first and second lumens 963 and 964, that communicate with the opening 931 for applying suction thereto. The suction dynamics at the opening 931 may be further modified by applying different amounts of suction to the first port 240 and the second port 241.

A blade 900 may be disposed at least partially within the first suction lumen 963. Further, the distal end 902 of the blade 900 may extend through the opening 931. Further, a suction tube 965 may be added to the second lumen 964 to enhance the suction force applied at or near the opening 931. In any event, tissue may be drawn toward the first lumen 963 and/or the second lumen 964 when suction is applied to one or both of suction ports 240, 241. The dual suction lumens 963, 964 may provide enhanced contact and suction of tissue in a liquid environment, such as that experienced during arthroscopic surgery. The two lumens 963, 964 may provide a reliable device capable of pulling in fibrous tissue and evacuating debris therethrough.

Referring to FIG. 24A, which illustrates a side view of a distal portion of the blade 900, the blade 900 may be rasped or include teeth 901 near its distal end 902. The teeth 901 may help improve tissue ablation by adding an optimized surface for friction to occur in a liquid environment. Additionally, while the blade 900 may be coupled to an ultrasonic transducer, such as one or more contained in the ultrasonic transducer assembly 114 (see FIG. 22), so that the blade 900 may experience ultrasonic vibrational motion, the blade 900 may also be coupled to a drive system configured to apply gross axial motion thereto, as described above, thereby enhancing the cutting ability of the blade 900. Further, in at least one embodiment and referring to FIG. 23, the blade's distal end 902 may be retracted into the hollow sheath 930 by the drive system such that the blade does not unintentionally cut tissue until desired, at which point the blade may be extended back through the opening 931.

Alternatively, other blade configurations may be employed. For example, referring to FIG. 24B, a blade 900' may contain a flat surface 901' near its distal end 902'. In such embodiments, the surface itself may generate enough friction, when ultrasonic vibrational motion is applied thereto, to cut tissue.

Figure 25:
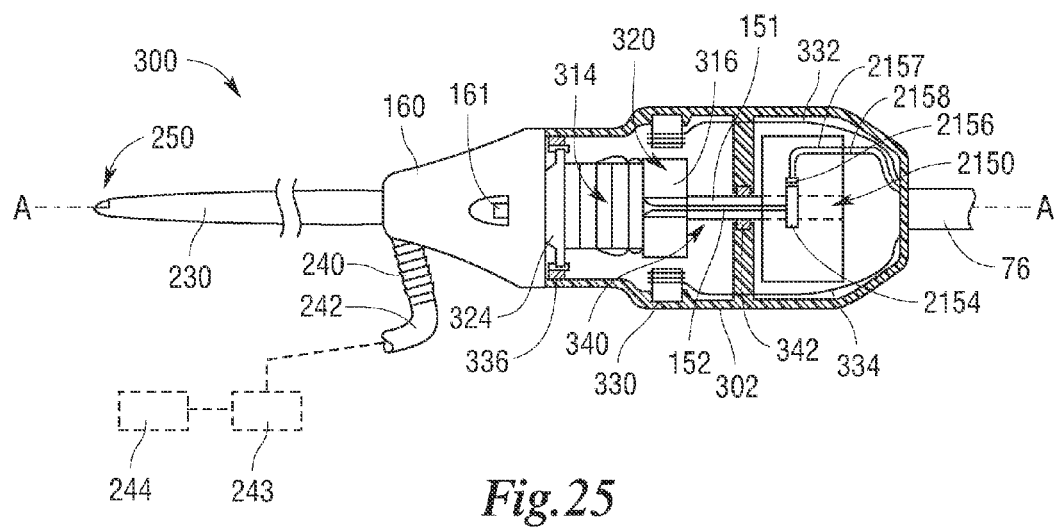
FIG. 25 is a partial cross-sectional view of a non-limiting embodiment of a surgical instrument employing a rotational drive system.
Figure 26:
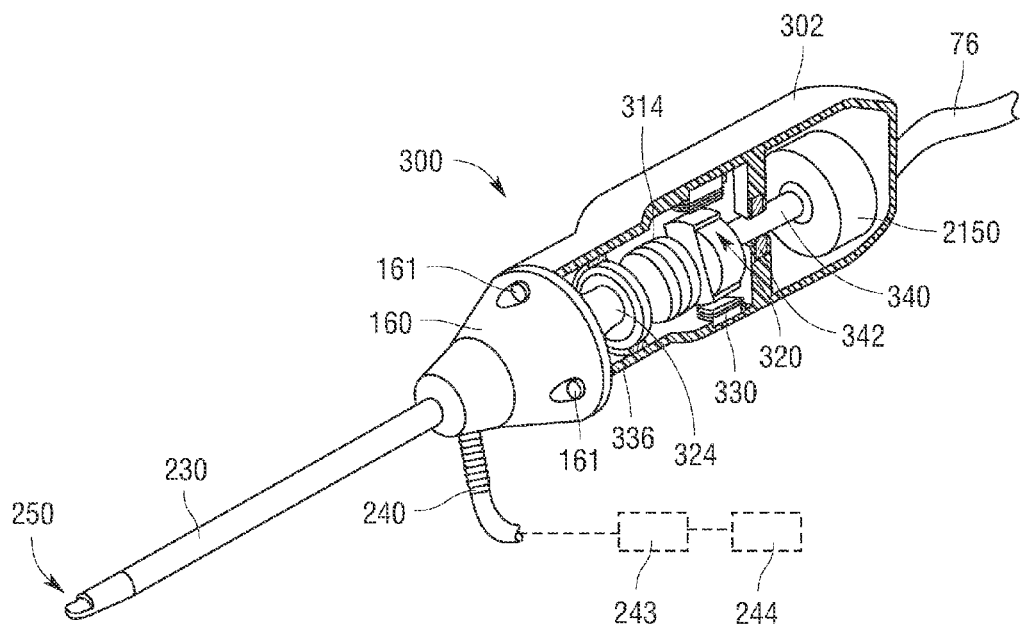
FIG. 26 is a perspective view of the surgical instrument of FIG. 25.

While some of the embodiments described above have disclosed gross axial motion of a blade to provide various advantages, similar advantages may be obtained with a surgical instrument that instead utilizes gross rotational motion of a blade. Focusing now on one non-limiting embodiment, FIGS. 25-26 illustrate another surgical instrument 300 wherein like numbers previously used to describe the various embodiments disclosed above are used to designate like components. In these embodiments, the surgical instrument 300 includes a housing 302 that houses a transducer assembly 314 that is attached to an ultrasonic horn 324. The ultrasonic horn 324 may be coupled to the proximal end of the blade 200, as discussed above. The ultrasonic horn 324 may be rotatably supported within the housing 302 by a distal bearing 336. A nosepiece 160 may be attached to the housing 302 by fasteners 161 in the manner described above.

In this embodiment, a drive system may be provided that communicates with the transducer assembly 314 to deliver rotational motions thereto such that the blade rotates with respect to the hollow sheath 230 when the drive system is activated. For example, the ultrasonic transducer assembly 314 may have magnets 316 embedded or otherwise attached thereto to form an integral motor rotor, generally designated as 320. A motor stator ring 330 is mounted within the housing 302 as shown. Conductors 332, 334 are attached to the motor stator ring 330 and pass through the common sheath 76 to be attached to the motor cable 33 in the control system 20 as described above. A hollow shaft 340 extends through the motor rotor 320 to form a passage for conductors 151, 152. Conductors 151, 152 are coupled to the ultrasonic transducer assembly 314 and an inner contact 2154. The inner contact 2154 is attached to a portion of the hollow shaft 340 that rotatably extends into a slip ring assembly 2150 that is also supported within the housing 302. The hollow shaft 340 is rotatably supported within the housing 302 by a proximal bearing 342. The slip ring assembly 2150 is fixed (i.e., non-rotatable) within the housing 302 and includes a fixed outer contact 2156 that is coupled to conductors 2157, 2158 that form a generator cable 14. When power is supplied to the motor stator 330, the rotor 320 and the integral ultrasonic transducer 314 are caused to rotate about axis A-A. Ultrasonic signals from the ultrasonic generator 12 are transferred to the inner contact 2154 by virtue of rotating contact or electrical communication between the inner contact 2154 and the outer contact 2156. Those signals are transmitted to the ultrasonic transducer assembly 314 by conductors 151, 152. A suction may be applied between the blade 200 and hollow sheath 230 through port 240. A collection receptacle 243 and source of suction 240 may be attached to the port 240 by tube 242. The distal end of the blade is exposed through a window in the distal end of the hollow sheath 230 at the distal portion 250 of the instrument to expose the blade to tissue as will be further discussed below.

Additional details regarding surgical instrument 300 and other embodiments of surgical instruments with rotating blades may be found in U.S. patent application Ser. No. 12/703,860, entitled ULTRASONIC SURGICAL INSTRUMENTS WITH ROTATING CUTTING IMPLEMENT, filed on even date herewith, which is incorporated herein by reference in its entirety.

In at least one embodiment, the distal portion of a surgical instrument may be configured to grip tissue that is being cut. Focusing now on one non-limiting embodiment, FIG. 27 illustrates an example of the distal portion 1050 of the surgical instrument wherein like numbers previously used to describe the various embodiments disclosed above are used to designate like components. The hollow sheath 1030 may include an opening 1031 therein that is positioned such that tissue may be drawn therethrough and into contact with the blade 1000. The opening 1031 may further include one or more teeth 1032 that are configured to grip tissue positioned within the opening 1031. Additionally, the opening 1031 may project away from the blade 1000, or otherwise be shaped to increase the surface area of the opening to increase suction force at the opening 1031 when suction is applied to the instrument, as described above. Thus, tissue "T", which is shown being drawn toward the opening 1031, may be better held by the instrument when the blade 1000 is ultrasonically activated and/or grossly translated or rotated. Holding or gripping the tissue T when the blade is cutting may be advantageous to prevent the tissue T from bypassing a cutting edge 1006 of the blade 1000.

The teeth 1032 may be annular ribs as shown in FIG. 27. Alternatively, referring to FIGS. 28-29, which show various teeth options, the teeth 1032 may be hooks 1032', fish-scale like tabs 1032", or a roughened surface (not shown). FIG. 29 shows the tissue T being gripped by the tabs 1032".

Figure 30:
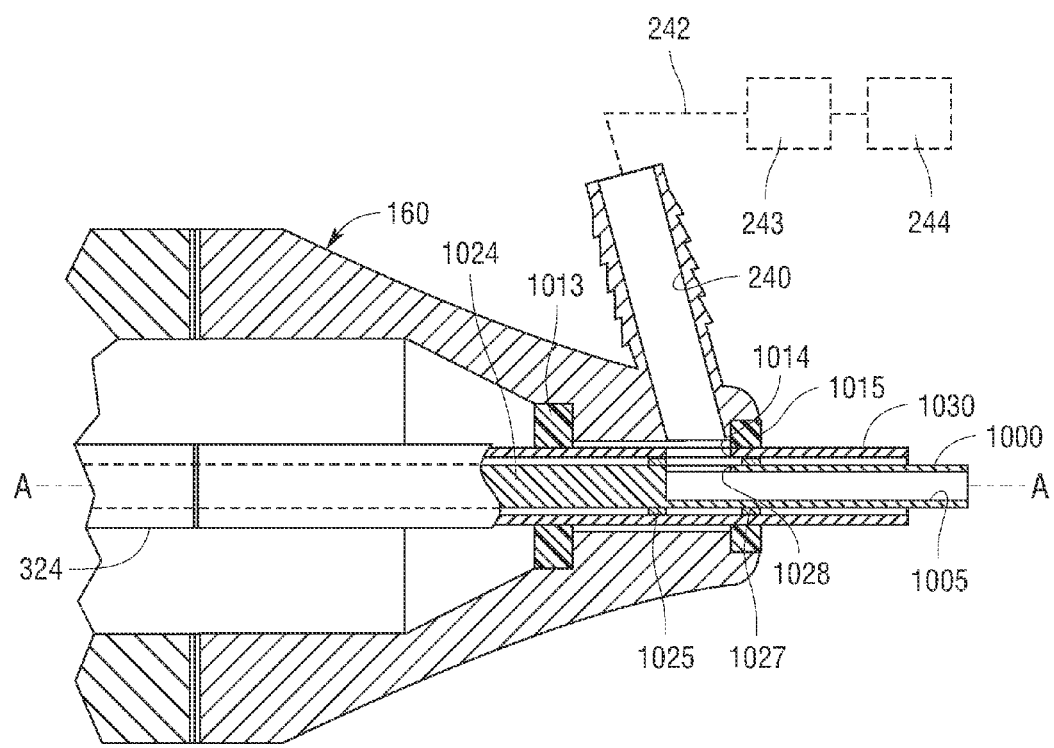
FIG. 30 is a side cross-section view of a nose piece and associated components of a surgical instrument, such as the surgical instrument of FIG. 27.

Further, as noted above, the blade may grossly rotate or translate with respect to the hollow shaft, by way a drive system as described above. Also, in at least one embodiment, the blade may be hollow and define a lumen 1005 therein through which suction may be applied to draw tissue toward and into contact with the blade 1000. In at least one embodiment, the suction port 240 (see FIGS. 25-26) may communicate exclusively with the lumen 1005. In other words, the suction path may be limited to the lumen 1005 and not include the space between the hollow sheath 1030 and the blade 1000. In more detail, referring to FIG. 30, which illustrates an embodiment of nosepiece 160 and various related components, the hollow sheath 1030 is supported within a hollow nosepiece 160 that has a suction port 240 therein. A flexible tube 242 may be attached to the suction port 240 and communicate with a collection receptacle 243 that is coupled to a source of suction, generally depicted as 244. The hollow sheath 1030 may be supported within the nosepiece 160 by a proximal seal 1013 and a distal seal 1015 which are located on each side of the suction port 240 and which serve to establish fluid tight seals therebetween. The hollow sheath 1030 is provided with at least one proximal opening 1014 in registration with the suction port 240 between the proximal seal 1013 and the distal seal 1015. In addition, the blade 1000 is rotatably supported within the hollow sheath 1030 by at least a proximal blade seal 1025 and a distal blade seal 1027. At least one blade discharge port 1028 may be provided through the lumen 1005 of the blade 1000 between the proximal blade seal 1025 and the distal blade seal 1027 to discharge into the at least one proximal sheath opening 1014.

In various embodiments, in a rotary surgical instrument, such as surgical instrument 300 described above, it may be desirable to reduce the blade mass to optimize rotational cutting speed. Thus, in at least one non-limiting embodiment, focusing now on FIGS. 31-32, a blade 1100 may be paddle shaped. FIG. 31 is a side view of a distal portion 1150 of a surgical instrument including the rotatable blade 1100 and FIG. 32 is a cross-section view of the distal portion 1150, taken along line 32-32. A hollow sheath 1130 may include opening 1131, as discussed above. The blade 1100 may be disposed at least partially within the hollow sheath 1130 and include a wide portion 1101 and a narrow portion 1102. The narrow portion 1102 may extend proximally and be coupled to the horn 324 (see FIG. 25). The wide portion 1102 of the blade 1100 may extend toward and/or into the opening 1131.

In at least one embodiment, referring to FIG. 32, the blade 1100 may include a concave surface or surfaces 1103 to further reduce rotational inertia as the blade 1100 rotates in a clockwise "CW" or counterclockwise "CCW" direction. Additionally, the concave surfaces 1103 may vary along the cross section of the blade 1100 to enhance the blade's cutting ability. Referring now to FIGS. 33A and 33B, the cross-section of blade 1100 at lines 33A-33A and 33B-33B, respectively, can be seen. The distal portion of the concave surfaces 1103 (see FIG. 33A) may be thicker and taller than the proximal portion of the same (see FIG. 33B). Alternatively, referring to FIG. 34, the mass of a blade 1100' may be reduced by forming a hole 1105 along the longitudinal axis of the blade 1100'. In at least one embodiment, the hole 1105 may be milled into the blade 1100'.

Figure 36:
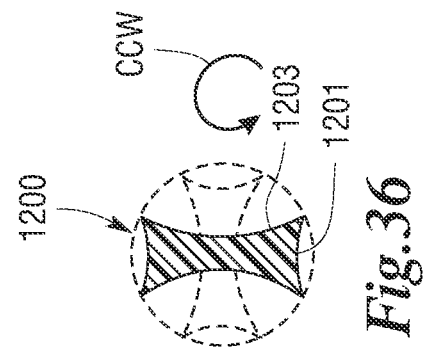
FIG. 36 is a cross-sectional view of the blade of FIG. 35, taken along line 36-36.
Figure 35:
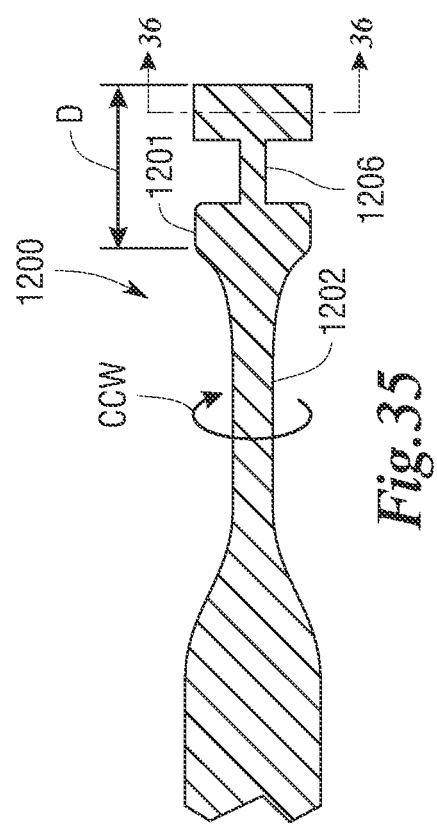
FIG. 35 is a side cross-sectional view of another non-limiting embodiment of a blade for a surgical instrument, such as the surgical instrument of FIG. 31.
Figure 37:
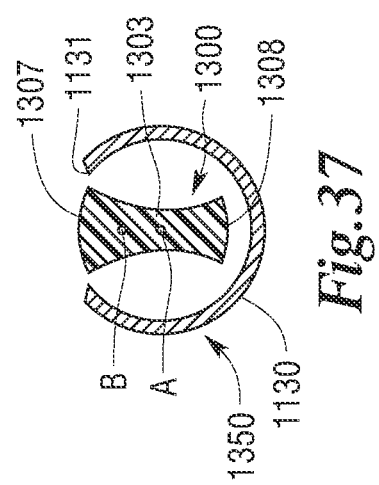
FIG. 37 is a front cross-sectional view of a distal portion of a non-limiting embodiment of a surgical instrument including a mass balanced blade.

In at least one embodiment, referring to FIGS. 35-36, the mass of a blade 1200 usable with hollow sheath 1130 described above, may be reduced by using a blade including a gap 1206 positioned such that it may align within the opening 1131 of the sheath 1130, see FIG. 31. Again, referring to FIG. 35, the blade 1200 may include a narrow portion 1202 and a wide portion 1201. The wide portion 1201 may further define the gap 1206 therein that may be positioned such that the gap 1206 is next to or coincident with the opening 1131, when the blade 1200 is used with sheath 1130, see FIG. 31. The length "D" of the wide portion 1201 may be such that the length D is at least as long as is the opening 1131, see FIG. 31. Again, as described above and referring to FIG. 36, the wide portion 1201 of the blade 1200 may include a concave surface 1203 to reduce blade mass. Alternatively, a blade may further reduce blade mass by incorporating a blade that is mass balanced such that it may have an elliptical center that is offset from the axis of rotation. For example, referring to FIG. 37, an axial or front cross-sectional view of a distal portion 1350 of a surgical instrument including a blade 1300 is shown positioned within the hollow sheath 1130, as described above. The blade 1300 may be configured to rotate about axis "A." However, the concave surface 1303 may not be symmetric about that axis. For example, a first side 1307 of the blade 1300 may be wider than a second side 1308. In such embodiments, the elliptical center "B" may be offset from the rotational axis A. Accordingly, the blade may be made from a non-homogenous material such that distribution of mass about the rotational axis A is balanced and the blade may rotate at high speeds without damaging itself or the hollow sheath 1130.

Alternative rotational blade configurations are possible. For example, referring to FIGS. 38-39, a non-limiting embodiment is provided in which a blade 1400 may include a screw surface 1403 positioned next to an opening 731 in a hollow sheath 730. The sheath 730 may be similar to the sheath 730 seen in FIG. 9 and discussed above. For example, the sheath 730 may also include a shearing plate 736 with a beveled shearing surface 735 positioned in the opening 731, as discussed above. Also as noted above, the beveled shearing surface 735 may be similar to a single tooth in that it provides a sharpened edge against which tissue may be cut. In any event, the screw surface 1403 may function like an auger and as the blade 1400 is rotated, the screw surface 1403 may pull tissue toward the shearing plate 736 to enhance the cutting of tissue.

Figure 40:
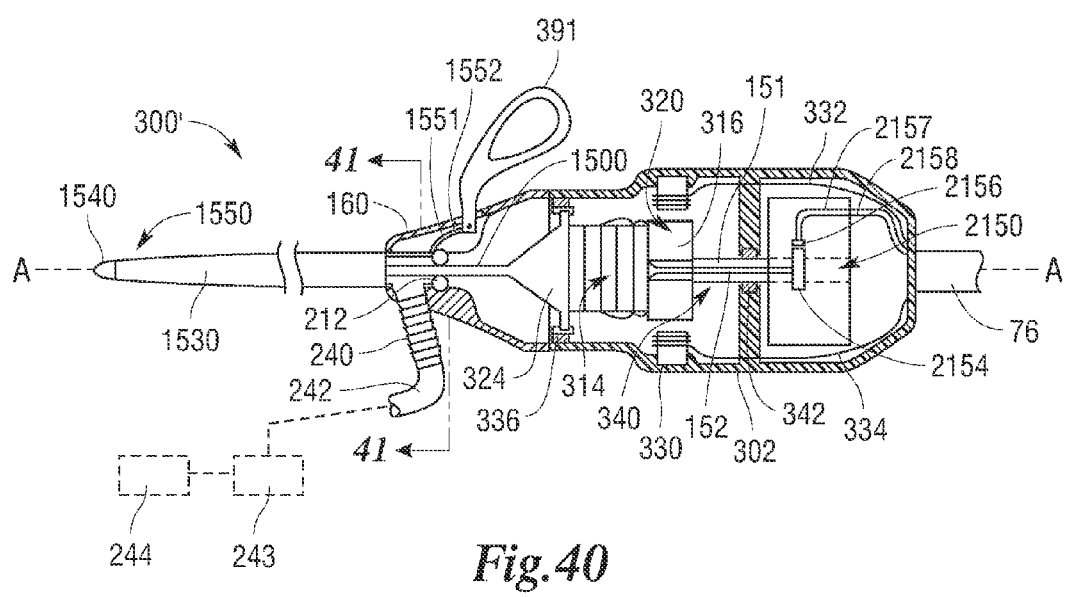
FIG. 40 is a partial cross-sectional view of a non-limiting embodiment of a surgical instrument including a movable tissue gripping member.

In various embodiments, tissue may be gripped by a movable tissue gripping member to enhance the cutting thereof. Focusing now on one non-limiting embodiment, FIGS. 40-43 illustrate another surgical instrument 300' wherein like numbers previously used to describe the various embodiments disclosed above are used to designate like components. FIG. 40 is a partial cross-sectional view of the surgical instrument 300'. The surgical instrument 300' may be similar to surgical 300 describe above and seen in FIG. 25, for example, except at least that it further includes a drive system including a trigger 391 pivotally coupled to the nosepiece 160 that is subsequently connected to and configured to cause a tissue gripping member 1550 to move with respect to a hollow sheath 1530 (see FIGS. 42A-42B). Additionally, as discussed above, the blade 1500 is configured to rotate at least partially within the hollow sheath 1530.

Figure 41:
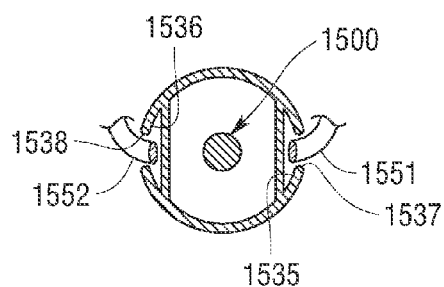
FIG. 41 is a cross-sectional view of a hollow sheath, cables, and a blade of the surgical instrument of FIG. 40, taken along line 41-41.

As noted above, the drive system may be configured to deliver axial motions to the tissue gripping member 1540 such that the tissue gripping member translates with respect to the hollow sheath 1530 when the drive system is activated. In more detail, focusing now on FIGS. 42A-42B, FIG. 42A is a perspective view of a distal portion 1550 of the surgical instrument 300' with the tissue gripping member 1540 shown in an extended position and FIG. 42B is a perspective view of the distal portion 1550 with the tissue gripping member 1540 shown in a retracted position. The hollow sheath 1530 may include a distal opening 1531 that opens towards the distal direction DD. Further, extending from the opening 1531 may be the tissue gripping member 1540. At least one and optionally two load-bearing cables 1551, 1552 may be coupled to the tissue gripping member 1540 and extend in the proximal direction PD therefrom. As used herein, a cable can include a solid core cable, a twisted wire cable, a chain, a band, a rope, etc., and any other load-bearing member. Inside the hollow sheath 1530, referring to FIG. 43, which shows a cross-section view of the hollow sheath 1530, cables 1551, 1552, and blade 1500, taken along line 43-43 in FIG. 42A, may be channels 1535, 1536 that are sized and configured to receive the cables 1535, 1536 therein. Although not shown, the channels may open at a distal opening (not shown) at or near the sheath's opening 1531. Referring still to FIG. 43, the blade 1500 may include concave surfaces 1503 as discussed above for facilitating the cutting of tissue; alternatively the blade may include a screw surface also as described above. Focusing back on FIGS. 40 and 41, FIG. 41 shows a cross-sectional view of the hollow sheath 1550, cables 1551, 1552, and blade 1500, taken along line 41-41, which is at or near the proximal end of the sheath 1550. As can be seen in FIG. 41, within the nosepiece 160, the cables 1551, 1552 may pass out of the channels 1535, 1536 of the hollow sheath 1530 by way of holes 1537, 1538 defined therein. The cables may be coupled to a trigger 391 which is pivotally mounted to the nosepiece. Accordingly, movement of the trigger 391 by a user may cause the cables 1551, 1552 and, subsequently, the tissue gripping member 1540 to axially move or translate with respect to the hollow sheath 1530.

The surgical instrument 300' may be used as follows. First, a user may manipulate the trigger 391 to extend the tissue gripping member 1540, as seen in FIG. 42. Next, the user may place tissue between the hollow sheath 1530 and the gripping member 1540. Optionally, suction may be applied to port 240 to assist in the positioning of the tissue. Then, the user may move the trigger 391 such that the gripping member 1540 retracts to a position like the one seen in FIG. 42B, thereby pulling tissue into the hollow sheath 1530 and into contact with the blade 1500. At the same time or after retracting the gripping member 1540, the user may activate the ultrasonic transducer assembly 314 such that ultrasonic vibrational motion is applied to the blade 1500. Optionally, power may also be supplied to the motor stator 330 such that the rotor 320, the integral ultrasonic transducer 314, and the blade 1500 are caused to rotate about axis A-A. The gripped tissue may therefore be cut by one or both of the ultrasonic vibrational motion and the gross rotational motion of the blade 1500. After cutting the tissue, the remnants may be suctioned out of the instrument 300' via port 240, as described above. The above exemplary steps may be repeated to cut additional tissue.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the various embodiments described herein will be processed before surgery. First, a new or used instrument is obtained and if necessary cleaned. The instrument can then be sterilized. In one sterilization technique, the instrument is placed in a closed and sealed container, such as a plastic or TYVEK® bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility. Sterilization can also be done by any number of ways known to those skilled in the art including beta or gamma radiation, ethylene oxide, and/or steam.

In various embodiments, an ultrasonic surgical instrument can be supplied to a surgeon with a waveguide and/or end effector already operably coupled with a transducer of the surgical instrument. In at least one such embodiment, the surgeon, or other clinician, can remove the ultrasonic surgical instrument from a sterilized package, plug the ultrasonic instrument into a generator, as outlined above, and use the ultrasonic instrument during a surgical procedure. Such a system can obviate the need for a surgeon, or other clinician, to assemble a waveguide and/or end effector to the ultrasonic surgical instrument. After the ultrasonic surgical instrument has been used, the surgeon, or other clinician, can place the ultrasonic instrument into a sealable package, wherein the package can be transported to a sterilization facility. At the sterilization facility, the ultrasonic instrument can be disinfected, wherein any expended parts can be discarded and replaced while any reusable parts can be sterilized and used once again. Thereafter, the ultrasonic instrument can be reassembled, tested, placed into a sterile package, and/or sterilized after being placed into a package. Once sterilized, the reprocessed ultrasonic surgical instrument can be used once again.

Although various embodiments have been described herein, many modifications and variations to those embodiments may be implemented. For example, different types of end effectors may be employed. Also, where materials are disclosed for certain components, other materials may be used. The foregoing description and following claims are intended to cover all such modification and variations.

Any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A surgical instrument, comprising:
   a hollow sheath;
   a translatable ultrasonic blade movably disposed at least partially within the hollow sheath, wherein the translatable ultrasonic blade is configured to vibrate and translate along a longitudinal axis relative to the hollow sheath;
   a first drive system comprising at least one ultrasonic transducer operably coupled to the translatable ultrasonic blade, wherein the at least one ultrasonic transducer is configured to generate longitudinal vibrations in the translatable ultrasonic blade when the first drive system is activated; and
   a second drive system, comprising:
      a motor; and
      a linear motion generator operably coupled to the motor and to the translatable ultrasonic blade, wherein the linear motion generator is configured to communicate with the at least one transducer to deliver gross axial motions to the translatable ultrasonic blade and to the at least one ultrasonic transducer when the second drive system is activated, and wherein the translatable ultrasonic blade and the at least one ultrasonic transducer is configured to translate along the longitudinal axis with respect to the hollow sheath when the second drive system is activated.

2. The surgical instrument of claim 1, further comprising:
   a plurality of openings in the hollow sheath;
   at least one tooth on the translatable ultrasonic blade; and
   a suction port communicating with the hollow sheath, wherein the suction port is configured to facilitate an application of suction to the plurality of openings such that tissue is drawn into the plurality of openings.

3. The surgical instrument of claim 1, wherein the hollow sheath comprises at least one opening, a first suction lumen, and a second suction lumen therein, wherein the first suction lumen and the second suction lumen communicate with the at least one opening for supplying suction thereto, and wherein the translatable ultrasonic blade is disposed at least partially within the first suction lumen.

4. The surgical instrument of claim 3, further comprising a first suction port communicating with the first suction lumen and a second suction port communicating with the second suction lumen.

5. The surgical instrument of claim 3, wherein the translatable ultrasonic blade extends through the at least one opening.

6. The surgical instrument of claim 1, wherein the hollow sheath further comprises a septum therein, wherein the septum includes a perforated portion.

7. The surgical instrument of claim 1, wherein the translatable ultrasonic blade further includes a lumen defined therein.

8. The surgical instrument of claim 1, wherein the hollow sheath comprises at least one opening including a beveled shearing surface.

9. A surgical instrument, comprising:
   a hollow sheath;
   a blade disposed at least partially within the hollow sheath;
   a first drive system comprising at least one ultrasonic transducer operably coupled to the blade; and
   a second drive system comprising a linear motion generator communicating with the at least one transducer to deliver gross axial motions to the blade and to the at least one ultrasonic transducer such that the blade and the at least one ultrasonic transducer translate with respect to the hollow sheath when the second drive system is activated, wherein the second drive system comprises a motor coupled to the linear motion generator, and wherein the linear motion generator comprises one of a rack-and-pinion mechanism, a slider-crank mechanism, a worm gear mechanism, a lead screw mechanism, and any combination thereof.

10. A surgical instrument, comprising:
    a hollow sheath;
    a blade disposed at least partially within the hollow sheath;
    a first drive system comprising at least one ultrasonic transducer operably coupled to the blade; and
    a second drive system comprising a linear motion generator communicating with the at least one ultrasonic transducer to deliver motions to the blade and to the at least one ultrasonic transducer, wherein the blade is configured to translate relative to the hollow sheath when the linear motion generator of the second drive system is activated, and wherein the second drive system comprises a trigger operably engaged with the at least one ultrasonic transducer.

11. A surgical instrument, comprising:
    a hollow sheath;
    a blade disposed at least partially within the hollow sheath, wherein the blade is configured to vibrate and translate along a longitudinal axis relative to the hollow sheath;
    a first drive system comprising at least one translatable ultrasonic transducer operably coupled to the blade, wherein the blade is configured to vibrate when the first drive system is activated; and
    a second drive system communicating with the at least one translatable ultrasonic transducer, wherein the second drive system comprises a linear motion generator, wherein the at least one translatable ultrasonic transducer is configured to translate relative to the second drive system and the blade is configured to translate relative to the hollow sheath when the linear motion generator of the second drive system is activated.

12. A surgical instrument, comprising:
    a hollow sheath;
    a movable drive assembly, comprising:
       an ultrasonic blade disposed at least partially within the hollow sheath; and
       at least one ultrasonic transducer operably coupled to the ultrasonic blade, wherein the at least one ultrasonic transducer is configured to generate longitudinal vibrations in the ultrasonic blade when the at least one ultrasonic transducer is activated; and
    a drive system operably engageable with the movable drive assembly, wherein the drive system comprises:
       a motor; and
       a linear motion generator operably coupled to the motor, wherein the linear motion generator is configured to longitudinally displace the ultrasonic blade and the at least one ultrasonic transducer relative to the hollow sheath when the motor is activated.

13. The surgical instrument of claim 12, wherein the drive system is configured to displace the ultrasonic blade and the ultrasonic transducer in a gross axial motion relative to the hollow sheath.

14. A surgical instrument, comprising:
    a hollow sheath;
    a movable drive assembly, comprising:
       a blade disposed at least partially within the hollow sheath, wherein the blade comprises a distal shearing surface and a proximal attachment portion; and
       at least one transducer operably coupled to the blade, wherein the transducer is directly attached to said proximal attachment portion; and a drive system operably engageable with the movable drive assembly, wherein the drive system comprises a linear motion generator configured to longitudinally displace the blade and the transducer relative to the hollow sheath, and wherein the drive system is directly attached to the proximal attachment portion.

* * * * *